United States Patent
Gurova

(10) Patent No.: US 10,386,370 B2
(45) Date of Patent: Aug. 20, 2019

(54) USE OF FACILITATES CHROMATIN TRANSCRIPTION COMPLEX (FACT) IN CANCER

(71) Applicant: Incuron, Inc., Buffalo, NY (US)

(72) Inventor: Katerina Gurova, Orchard Park, NY (US)

(73) Assignee: Incuron, Inc., Buffalo, NY (US)

( * ) Notice: Subject to any disclaimer, the term of this patent is extended or adjusted under 35 U.S.C. 154(b) by 19 days.

(21) Appl. No.: 14/766,693

(22) PCT Filed: Feb. 11, 2014

(86) PCT No.: PCT/US2014/015854
§ 371 (c)(1),
(2) Date: Aug. 7, 2015

(87) PCT Pub. No.: WO2014/124454
PCT Pub. Date: Aug. 14, 2014

(65) Prior Publication Data
US 2016/0033515 A1 Feb. 4, 2016

Related U.S. Application Data

(60) Provisional application No. 61/883,802, filed on Sep. 27, 2013, provisional application No. 61/763,266, filed on Feb. 11, 2013.

(51) Int. Cl.
*G01N 33/574* (2006.01)

(52) U.S. Cl.
CPC ... *G01N 33/57496* (2013.01); *G01N 2333/47* (2013.01); *G01N 2333/4703* (2013.01)

(58) Field of Classification Search
None
See application file for complete search history.

(56) References Cited

U.S. PATENT DOCUMENTS

| 7,169,802 | B2 | 1/2007 | Hudkins et al. |
| 2005/0143442 | A1 | 6/2005 | Hudkins et al. |
| 2011/0183336 | A1 | 7/2011 | Gray et al. |
| 2014/0066465 | A1 | 3/2014 | Stark et al. |
| 2015/0045406 | A1 | 2/2015 | Gudkov et al. |

FOREIGN PATENT DOCUMENTS

| DE | 2715680 | 10/1978 |
| WO | 2004035580 | 4/2004 |
| WO | 2008008155 | 1/2008 |
| WO | 2009143290 | 11/2009 |
| WO | 2010009171 | 1/2010 |
| WO | 2010042445 | 4/2010 |
| WO | 2013148864 | 10/2013 |

OTHER PUBLICATIONS

Van Diest et al. (J. Clin. Pathol. 50: 801-804, 1997).*
Di Bussolo, V. et al., "Curaxins: A New Family of Non-Genotoxic Multitargeted Anticancer Agents," ChemMedChern, vol. 6, No. 12, pp. 2133-2136 (Oct. 28, 2011).
Garcia, H. et al., "Expression of FACT in mammalian tissues suggests its role in maintaining of undifferentiated state of cells," Oncotarget, Impact Journals LLC, United States, vol. 2, No. 10, pp. 1-14 (Oct. 1, 2011).
Gasparian, A. V. et al., "Curaxins: Anticancer Compounds that Simultaneously Suppress NF-kappa B and Activate p53 by Targeting FACT," Science Translational Medicine, vol. 3, No. 95, pp. 96-107 (Aug. 2011).
Koman, I. E. et al., "Targeting FACT Complex Suppresses Mammary Tumorigenesis in Her2/neu Transgenic Mice," Cancer Prevention Research, American Association for Cancer Research, United States, vol. 5, No. 8, pp. 1025-1035 (Aug. 1, 2012).
Pieters et al., "Reciprocal Template Effects in Bisubstrate Systems: A Replication Cycle," Tetrahedron, vol. 51, No. 2, pp. 485-498 (May 22, 1994).
Belotserkovskaya et al., "FACT Facilitates Transcription-Dependent Nucleosome Alteration," Science, vol. 301, pp. 1090-1093 (Aug. 22, 2003).
Garcia et al., "Facilitates Chromatin Transcription Complex Is an 'Accelerator' of Tumor Transformation and Potential Marker and Target of Aggressive Cancers," Cell Reports (2013) http://dx.doi.org/10.1016/j.celrep.2013.06.013.
International Search Report, PCT/US14/15854, dated May 13, 2014, 3 pages.

* cited by examiner

*Primary Examiner* — Alana Harris Dent
(74) *Attorney, Agent, or Firm* — Morgan, Lewis & Bockius LLP

(57) ABSTRACT

The present invention relates to, inter alia, measuring of at least one component of the facilitates chromatin transcription complex (FACT) for evaluating a tumor, including, for example, determining the aggressiveness of a tumor and directing treatment.

9 Claims, 16 Drawing Sheets ically, there is a need for methods that can direct a healthcare provider's treatment plan with a cancer patient, based on knowledge of characteristics of a patient's tumor.

USE OF FACILITATES CHROMATIN TRANSCRIPTION COMPLEX (FACT) IN CANCER

PRIORITY

The present application is a U.S. national stage of International Patent Application No. PCT/US2014/015854, filed Feb. 11, 2014, which claims priority to U.S. Provisional Application 61/763,266, filed Feb. 11, 2013 and U.S. Provisional Application 61/883,802, filed Sep. 27, 2013, the contents of all of which are hereby incorporated by reference in their entireties.

FIELD OF THE INVENTION

The present invention relates to, in part, methods that are useful in evaluating tumors in human samples and methods for selecting personalized treatment regimens.

BACKGROUND

A major limitation of current treatments for cancer is the selection of appropriate active agents for a patient. It is common that sub-optimal chemotherapy is provided to a patient, resulting in unsuccessful treatment, including death, disease progression, unnecessary toxicity, and higher health care costs. Further, some patients respond better without chemotherapy, using, for example, neoadjuvant or adjuvant therapy with surgery.

Assays to individualize and optimize cancer treatment, such as chemoresponse assays, have been developed to predict the potential efficacy of chemotherapy agents for a given patient prior to their administration. However, use of such assays is not widespread due, in-part, to difficulties in interpreting the data in a clinically meaningful way. For example, many such assays are thought to be unsuitable for providing accurate estimations of patient survival with particular treatment regimens (see. e.g., Fruehauf et al., Endocrine-Related Cancer 9:171-182 (2002)).

Therefore, there remains a need for methods that are useful for evaluating cancer and related diseases. Specifically, there is a need for methods that can direct a healthcare provider's treatment plan with a cancer patient, based on knowledge of characteristics of a patient's tumor.

BRIEF DESCRIPTION OF THE INVENTION

Accordingly, the present invention relates to methods for evaluating cancer, including, for example, methods for determining the aggressiveness of a cancer and the use of such information to guide treatment of a cancer patient.

In one aspect, the present invention provides a method for evaluating a tumor comprising measuring a presence, absence, or level of at least one component of facilitates chromatin transcription complex (FACT) in a human subject tumor specimen (including, for example, a biopsy) or cells cultured therefrom which, optionally, further comprises the step of classifying the subject into a high or low risk group based on the presence, absence, or level of at least one component of FACT. In some embodiments, the percentage of malignant cells expressing FACT is quantified and used to classify patients in low and high risk groups.

In one aspect, the present invention provides a method for evaluating a tumor cell comprising measuring a presence, absence, or level of at least one component of facilitates chromatin transcription complex (FACT) in a human subject tumor specimen (including, for example, a biopsy) or cells cultured therefrom which, optionally, further comprises the step of classifying the tumor cell as comprising a cancer stem cell based on the presence of at least one component of FACT.

In another aspect, the present invention provides for a method for treating cancer comprising administering an effective amount of an anti-cancer agent to a human subject wherein the cancer is characterized by presence, absence, or level of at least one component of facilitates chromatin transcription complex (FACT) in the human subject's tumor specimen or cells cultured therefrom. In another aspect, the present invention provides for a use of an anti-cancer agent for the treatment of a cancer, wherein the cancer is characterized as FACT$^+$.

In still another aspect, the present invention provides for a method for treating cancer, comprising (a) measuring a presence, absence, or level of at least one component of facilitates chromatin transcription complex (FACT) in a human subject tumor specimen (for example, in the malignant component of the specimen) or cells cultured therefrom; (b) classifying the subject into a high or low risk group based on the presence, absence, or level of at least one component of FACT (for example, in the malignant component of the specimen); and (c) administering an effective amount of a therapy to human subjects scoring as FACT$^+$. In another aspect, the present invention provides for a use of an therapy for the treatment of a cancer, comprising (a) measuring a presence, absence, or level of at least one component of facilitates chromatin transcription complex (FACT) in a human subject tumor specimen (for example, in the malignant component of the specimen) or cells cultured therefrom; (b) classifying the subject into a high or low risk group based on the presence, absence, or level of at least one component of FACT (for example, in the malignant component of the specimen); and (c) administering an effective amount of the therapy to human subjects scoring as FACT$^+$.

The details of the invention are set forth in the accompanying description below. Although methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs.

BRIEF DESCRIPTION OF THE DRAWINGS

FIG. 1A shows normal and immortalized fibroblasts have comparable levels of FACT subunits. Western blotting of extracts of tumor (HT1080), normal human (WI38) or mouse (MEFwt) fibroblasts and human fibroblasts immortalized with enzymatic subunit of telomerase (WI38-T) or mouse fibroblasts from p53 knockout animals (MEFp53KO) probed with indicated antibodies.

FIG. 1B shows expression of mutant H-Ras12V oncogene in immortalized human BJ fibroblasts is accompanied by elevation of FACT subunits levels. Western blotting of extracts of BJ cells with tamoxifen (TMX) regulated expression of H-Ras12V.

FIG. 1C shows SSRP1 is increased in foci formed by cells transformed with H-RasV12 oncogene. MEFp53KO cells were infected with lentivirus with H-RasV12 cDNA or control empty vector and allowed to grow until confluency and foci formation. Immunofluorescent staining with SSRP1 antibodies (green) of different density areas on plates transduced with H-RasV12 virus or control empty virus. DNA was counterstained with Hoechst33342 (blue).

FIG. 2A. shows immunofluorescent (IF) staining of primary (184, 240 L), immortal (184Dp16sMY, 240Lp16sMY, 184B5) and fully transformed (184FMY2, 184AA3) cells with antibodies to SSRP1. IF and phase contrast images of the same fields of view are shown.

FIG. 2B shows Western blotting of extracts of the same cells probed with the indicated antibodies.

FIG. 2C shows qPCR analysis of SSRP1 and SPT16 mRNA in the cells of 184 panel.

FIG. 3A shows a dotplot of all analyzed samples (X-axis) with normalized expression levels (Y-axis) in an anatomically and pathologically ordered fashion. Colored samples (colors according to the legend at the top) are those where the tissue type has an expression level 1 standard deviation higher than the average expression of all tissues of the same type (healthy, cancer, or other disease), or the 90th percentile of expression in the tissue is equal or higher than 2 times interquartile range plus the 75th percentile of the same type. However, no anatomy or cancer type is colored if there are less than ten datapoints per tissue type.

FIG. 3B shows SSRP1 mRNA levels in various tumor types.

FIG. 4A shows lung cancer.

FIG. 4B. shows colon cancer.

FIG. 4C. shows pancreatic cancer.

FIG. 4D. shows breast cancer.

FIGS.

FIG. 5A shows box-whisker plots of SSRP1 mRNA levels in samples of normal breast (1), breast ductal (2), lobular (3) medullar (4) and other (5) carcinomas.

FIG. 5B shows breast cancer samples categorized based on gene expression signature;

FIG. 5C shows tumor samples of different grades and stages. P-value of Mann-Whitney-Wilcoxon test between indicated samples are shown. P-values>0.05 are not shown FIG. 5D shows a comparison of the proportion of SSRP1 positive samples among patients within different categories of breast cancer based on IHC staining. P-values of exact Fisher chi-square test between different categories are shown.

FIG. 6A shows all cancers patients analyzed.

FIG. 6B shows lung cancer patients.

FIG. 6C shows pancreatic ductal patients.

FIG. 7A shows methylene blue staining.

FIG. 7B shows the colony number of cells transuded with the indicated lentiviral shRNA and selected at the presence of puromycin for RCC45 and NKE.

FIG. 7C shows the numbers of cells transduced with the indicated lentiviral shRNA and selected at the presence of puromycin for MCF7 and MCF10A.

FIG. 7D-F show levels of FACT subunits in cells shown on panel 7A after puromycin selection detected using western blotting.

FIG. 7G shows distribution of cells with high and low levels of SSRP1 protein detected using immunofluorescent staining among HT1080 cells 120 and 144 hrs after transduction with shRNA to SSRP1 (upper panels). Three lower panels show DNA content in HT1080 cells transduced with shRNA to GFP or SSRP1. Cells with high and low levels of SSRP1 were analyzed separately.

FIG. 7H shows EDU incorporation if different cells 3 days after transduction with the indicated lentiviral shRNAs.

FIG. 7I shows proportions of dead cells detected using Annexin V and propidium iodide staining (double positive) among HT1080 cells 5 days after transduction with the indicated lentiviral shRNAs.

DETAILED DESCRIPTION OF THE INVENTION

Figures 1A, 1B, 1C:
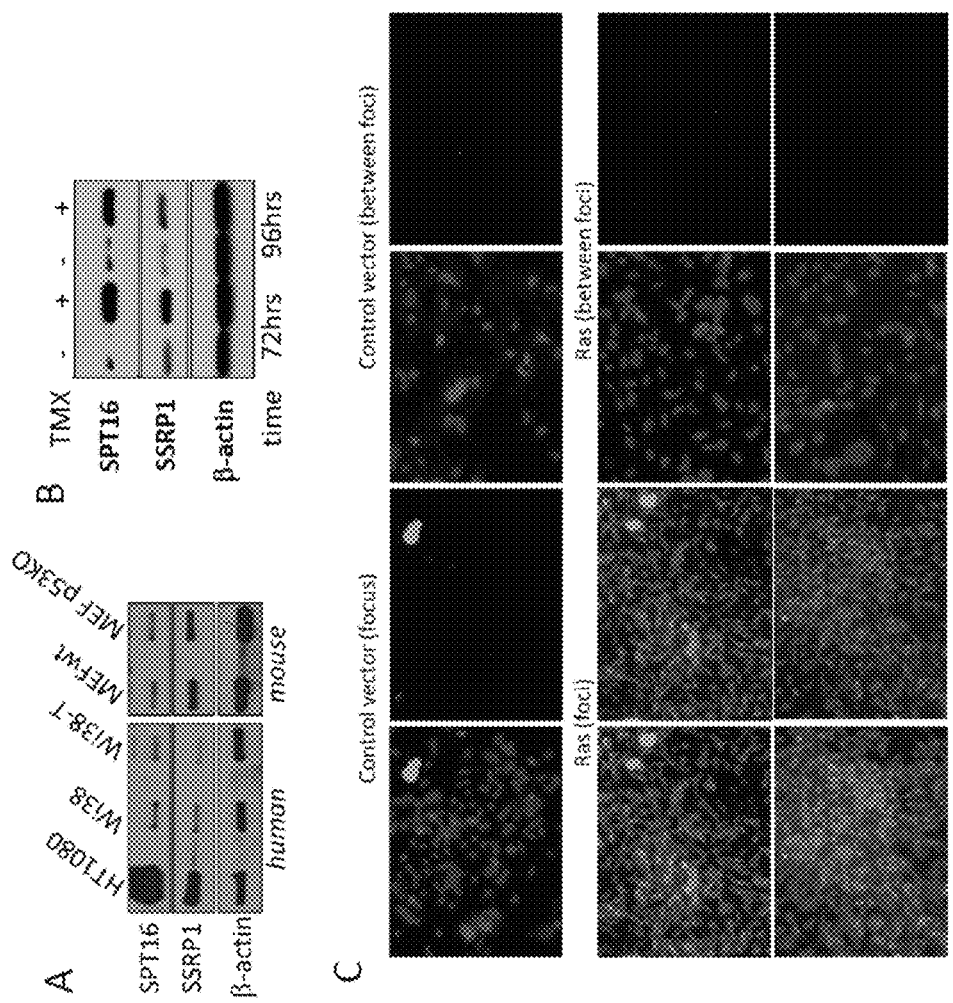
FIGS. 1A, 1B, and 1C show that FACT is elevated upon in vitro transformation, but not immortalization of human and mouse fibroblast cells.

The present invention is based, in part, on the discovery that presence of facilitates chromatin transcription complex (FACT) in malignant cells is useful for evaluating a tumor, including, for example, providing an indication of the aggressiveness of a tumor, the likelihood that a tumor is resistant to conventional drugs, and/or likely to recur after treatment, and therefore driving patient treatment decisions.

In one aspect, the present invention provides a method for evaluating a tumor comprising measuring a presence, absence, or level of at least one component of facilitates chromatin transcription complex (FACT) in a human subject tumor specimen (including, for example, a biopsy) or cells cultured therefrom which, optionally, further comprises the step of classifying the subject into a high or low risk group based on the presence, absence, or level of at least one component of FACT. In some embodiments, the tumor specimen is scored as FACT$^+$ or FACT$^-$ based on the relative level of FACT in the malignant cells particularly.

In another aspect, the present invention provides for a method for treating cancer comprising administering an effective amount of an anti-cancer agent to a human subject wherein the cancer is characterized as FACT$^+$. In another aspect, the present invention provides for a use of an anti-cancer agent for the treatment of a cancer, wherein the cancer is characterized by presence, absence, or level of at least one component of facilitates chromatin transcription complex (FACT) in the human subject's tumor specimen, or in the malignant cells, or cells cultured therefrom.

In still another aspect, the present invention provides for a method for treating cancer, comprising (a) measuring a presence, absence, or level of at least one component of facilitates chromatin transcription complex (FACT) in a human subject tumor specimen or cells cultured therefrom; (b) classifying the subject into a high or low risk group based on the presence, absence, or level of at least one component of FACT; and (c) administering an effective amount of a therapy to the human subject. In another aspect, the present invention provides for a use of an therapy for the treatment of a cancer, comprising (a) measuring a presence, absence, or level of at least one component of facilitates chromatin transcription complex (FACT) in a human subject tumor specimen or cells cultured therefrom; (b) classifying the subject into a high or low risk group based on the presence, absence, or level of at least one component of FACT; and (c) administering an effective amount of the therapy to the human subject. In some embodiments, the patient is classified as FACT$^+$ or FACT$^-$ as described herein and this classification is used to determine this patient's treatment.

In one embodiment, the evaluation comprises any one of diagnosis, prognosis, and response to treatment.

In another embodiment, the tumor is one or more of a primary or recurrent tumor or a metastatic lesion. In some embodiments, the tumor is any one of breast, prostate, pancreatic, lung, liver, kidney, bladder, colorectal, ovarian, cervical, head and neck, skin, central and peripheral nervous system.

In still another embodiment, the component of FACT comprises one or more of SSRP1 and SPT16.

In another embodiment, the measurement comprises evaluating a presence, absence, or level of a protein. In another embodiment, the measurement comprises evaluating a presence, absence, or level of expression of a nucleic acid encoding a component of FACT (e.g. PCR or nucleic acid hybridization assay). In some embodiments, the measurement comprises the use of an agent that specifically binds to one of SSRP1 and SPT16 protein and the agent may be, for example, an antibody. In various embodiments, the measurement of one or more of SSRP1 and SPT16 protein levels is any of immunohistochemical staining, western blotting, in cell western, immunofluorescent staining, ELISA, and fluorescent activating cell sorting (FACS).

In some embodiments, the human tumor specimens is a biopsy and/or is any one of a fresh tissue sample, frozen tumor tissue specimen, cultured cells (e.g. primary cultures from tumor specimens, circulating tumor cells), and a formalin-fixed paraffin-embedded tumor tissue specimen.

In another embodiment, the high or low risk classification is predictive of a positive response to and/or benefit from neoadjuvant and/or adjuvant chemotherapy or a non-responsiveness to and/or lack of benefit from neoadjuvant and/or adjuvant chemotherapy.

In still another embodiment, the high risk classification comprises a high level of cancer aggressiveness, wherein the aggressiveness is characterizable by one or more of a high tumor grade, aggressive histological subtypes, low overall survival, high probability of metastasis, and the presence of a tumor marker indicative of aggressiveness.

In still another embodiment, the low risk classification comprises a low level of cancer aggressiveness, wherein the aggressiveness is characterizable by one or more of a low tumor grade, high overall survival, less aggressive histological subtypes, low probability of metastasis, and the absence and/or reduction of a tumor marker indicative of aggressiveness.

In another embodiment, the high risk classification is indicative of and directs providing of neoadjuvant and/or adjuvant therapy. In another embodiment, a patient with a high risk classification is provided neoadjuvant and/or adjuvant therapy.

In another embodiment, the low risk classification is indicative of and directs withholding of neoadjuvant and/or adjuvant therapy. In another embodiment, a patient with a low risk classification is not provided neoadjuvant and/or adjuvant therapy.

In another aspect, the present invention provides a method for evaluating a tumor cell comprising measuring a presence, absence, or level of at least one component of facilitates chromatin transcription complex (FACT) in the malignant cells of a human subject tumor specimen (including, for example, a biopsy) or cells cultured therefrom which, optionally, further comprises the step of classifying the tumor cell as comprising a cancer stem cell based on the presence of at least one component of FACT.

In another embodiment, the tumor is one or more of a primary or recurrent tumor or a metastatic lesion. In some embodiments, the tumor is any one of breast, prostate, pancreatic, lung, liver, kidney, bladder, colorectal, ovarian, cervical, head and neck, skin, central and peripheral nervous system.

In still another embodiment, the component of FACT comprises one or more of SSRP1 and SPT16.

In another embodiment, the measurement comprises evaluating a presence, absence, or level of a protein. In another embodiment, the measurement comprises evaluating a presence, absence, or level of expression of a nucleic acid. In some embodiments, the measurement comprises the use of an agent that specifically binds to one of SSRP1 and SPT16 protein and the agent may be, for example, an antibody. In various embodiments, the measurement of one or more of SSRP1 and SPT16 protein levels is any of immunohistochemical staining, western blotting, in cell western, immunofluorescent staining, ELISA, and fluorescent activating cell sorting (FACS).

In some embodiments, the human tumor specimen is a biopsy and/or is any one of a frozen tumor tissue specimen, cultured cells (e.g. primary cultures from tumor specimens, circulating tumor cells), and a formalin-fixed paraffin-embedded tumor tissue specimen.

In some embodiments, FACT is a surrogate marker for cancer stem cells that can be used as a substitute for or supplement to known markers for such cells. Such use, in some embodiments, compliments the other uses of FACT for tumor evaluation described herein (e.g. as an indicator of tumor aggressiveness).

In some embodiments, the classification of the tumor cell type as comprising a cancer stem cell via FACT detection is indicative of a cancer type (e.g. cancer stem cell) that displays resistance to conventional chemotherapy. In some embodiments, a patient with a tumor that is classified as comprising a cancer stem cell via FACT detection is provided chemotherapy that is directed to cancer stem cells and/or known to be effective against cancer stem cells.

In some embodiments, the classification of the tumor cell type as comprising a cancer stem cell via FACT detection is indicative of a cancer type that is likely to relapse. In some embodiments, a detection of FACT in a patient that has been treated for a tumor may direct further monitoring post-treatment. In some embodiments, the detection of FACT in a patient that has been treated for a tumor may direct adjuvant or neoadjuvant therapy because of the likelihood of relapse.

The FAcilitates Chromatin Transcription (FACT) complex is a heterodimer of two subunits: an 80 kDa subunit and a 140 kDa subunit. These subunits are Structure Specific Recognition Protein 1 (SSRP1) and Suppressor of Ty (SPT16 or SUPT16H). As used herein, FACT refers to the heterodimer of SSRP1 and SPT16, or the individual SSRP1 and SPT16 subunits. Without wishing to be bound by theory, FACT is involved in chromatin remodeling through modulating of nucleosome stability. FACT may be involved in many processes involving chromatin, such as, for example, transcription, replication, recombination, DNA damage, and repair. FACT interacts specifically with histones H2A/H2B to effect nucleosome disassembly and transcription elongation. Curaxins (e.g. Curaxin-137), small molecules which have broad anti-cancer activity in different models of cancer (See International Patent Publication No. WO 2010/042445, the contents of which are hereby incorporated by reference in their entirety), cause functional inactivation of FACT (See Gasparian, et al. Sci. Trans. Med. 3: 95ra74 (2011), the contents of which are hereby incorporated by reference in their entirety).

The protein encoded by the gene of structure specific recognition protein 1 (SSRP1) (mRNA in humans: NM_003146.2, the sequence is hereby incorporated by reference in its entirety, mRNA in mouse: NM_001136081.1, the sequence is hereby incorporated by reference in its entirety) is a subunit of a heterodimer that, along with SPT16, forms FACT. SSRP1 is the 80 kDa subunit. FACT and cisplatin-damaged DNA may be crucial to the anticancer mechanism of cisplatin. SSRP1 encoded protein (in humans: NP_003137.1, the sequence is hereby incorporated by reference in its entirety, in mouse: NP_001129553.1, the sequence is hereby incorporated by reference in its entirety) contains a high mobility group box which, without wishing to be bound by theory, may constitutes the structure recognition element for cisplatin-modified DNA. SSRP1 is also a component of a CK2-SPT16-SSRP1 complex which forms following UV irradiation, comprising SSRP1, SUPT16H, CSNK2A1, CSNK2A2 and CSNK2B. SSRP1 has been shown to interact with NEK9, a serine/threonine-protein knish. SSRP1 protein also functions as a co-activator of the transcriptional activator p63 (including, for example, isoform gamma of TP63). SSRP1 enhances the activity of full-length p63, but it has no effect on the N-terminus-deleted p63 (DeltaN-p63) variant. SSRP1 also interacts with FYTTD1/UIF and SRF.

SPT16 (SUPT16H) is a protein that in humans is encoded by the SUPT16H gene (mRNA in humans: NM_007192.3, the sequence is hereby incorporated by reference in its entirety, mRNA in mouse: NM_033618.3, the sequence is hereby incorporated by reference in its entirety). The SPT16 protein (in humans: NP_009123.1, the sequence is hereby incorporated by reference in its entirety, in mouse: NP_291096.2, the sequence is hereby incorporated by reference in its entirety) is the 140 kDa subunit in the FACT complex. SPT16 is also a component of a CK2-SPT16-SSRP1 complex which forms following UV irradiation, comprising SSRP1, SUPT16H, CSNK2A1, CSNK2A2 and CSNK2B. Additionally, SPT16 is a component of the WINAC complex, comprising, at least, SMARCA2, SMARCA4, SMARCB1, SMARCC1, SMARCC2, SMARCD1, SMARCE1, ACTL6A, BAZ1B/WSTF, ARID1A, SUPT16H, CHAF1A and TOP2B. SPT16 has been shown to interact with BAZ1B, a tyrosine-protein kinase. SPT16 also interacts with NEK9, general transcription factor IIE subunit 2 (GTF2E2), and binds to histone H2A-H2B.

In various aspects, the present invention comprises evaluating a tumor. In various embodiments, the evaluation may be selected from diagnosis, prognosis, and response to treatment.

Diagnosis refers to the process of attempting to determine or identify a possible disease or disorder, such as, for example, cancer. Prognosis refers to the predicting of a likely outcome of a disease or disorder, such as, for example, cancer. A complete prognosis often includes the expected duration, the function, and a description of the course of the disease, such as progressive decline, intermittent crisis, or sudden, unpredictable crisis. Response to treatment is a prediction of a patient's medical outcome when receiving a treatment. Responses to treatment can be, by way of non-limiting example, pathological complete response, survival, and probability of recurrence.

In one embodiment, the high or low risk classification is predictive of a positive response to and/or benefit from neoadjuvant and/or adjuvant chemotherapy or a non-responsiveness to and/or lack of benefit from neoadjuvant and/or adjuvant chemotherapy.

In certain embodiments, neoadjuvant chemotherapy, refers to chemotherapy to shrink and/or downgrade the tumor prior to any surgery. Thus, as used herein, the term neoadjuvant chemotherapy means chemotherapy administered to cancer patients prior to surgery. Types of cancers for which neoadjuvant chemotherapy is commonly considered include, for example, breast, colorectal, ovarian, cervical, bladder, and lung.

Adjuvant therapy, also called adjuvant care, is treatment that is given in addition to the primary, main or initial treatment. By way of non-limiting example, adjuvant therapy may be an additional treatment (e.g. chemotherapy) usually given after surgery where all detectable disease has been removed, but where there remains a statistical risk of relapse due to occult disease.

In various embodiments, the invention provides for FACT and/or SSRP1 and/or SPT6-based tumor evaluation and classification of tumors into a high and low risk group. In various embodiments, FACT and/or SSRP1 and/or SPT16 is measured in a patient's specimen, including, for example, sorting/counting between normal and malignant cells and quantifying the number of malignant cells expressing FACT and/or SSRP1 and/or SPT16, for example, as a percent. In various embodiments, such measurements may assess a proximity of staining for FACT and/or SSRP1 and/or SPT16. In various embodiments, measurements may be computer-implemented.

In some embodiments, the high risk classification comprises a high level of cancer aggressiveness, wherein the aggressiveness is characterizable by one or more of a high tumor grade, aggressive histological subtypes, low overall survival, high probability of metastasis, and the presence of a tumor marker indicative of aggressiveness.

In still another embodiment, the low risk classification comprises a low level of cancer aggressiveness, wherein the aggressiveness is characterizable by one or more of a low tumor grade, less aggressive histological subtypes, high overall survival, low probability of metastasis, and the absence and/or reduction of a tumor marker indicative of aggressiveness.

Tumor grade is a system used to classify cancer cells in terms of how abnormal they look under a microscope and how quickly the tumor is likely to grow and spread. Many factors are considered when determining tumor grade, including the structure and growth pattern of the cells. The specific factors used to determine tumor grade may vary with each type of cancer and are known in the art.

Histologic grade, also called differentiation, refers to how much the tumor cells resemble normal cells of the same tissue type. Nuclear grade refers to the size and shape of the nucleus in tumor cells and the percentage of tumor cells that are dividing.

Based on the microscopic appearance of cancer cells, pathologists commonly describe tumor grade by four degrees of severity: Grades 1, 2, 3, and 4. The cells of Grade 1 tumors resemble normal cells, and tend to grow and multiply slowly. Grade 1 tumors are generally considered the least aggressive in behavior. Conversely, the cells of Grade 3 or Grade 4 tumors do not look like normal cells of the same type. Grade 3 and 4 tumors tend to grow rapidly and spread faster than tumors with a lower grade. The American Joint Committee on Cancer recommends the following guidelines for grading tumors: GX-grade cannot be assessed (Undetermined grade); G1-well-differentiated (Low grade); G2-moderately differentiated (Intermediate grade); G3-poorly differentiated (High grade); and G4-undifferentiated (High grade).

Grading systems are different for each type of cancer. For example, pathologists use the Gleason system to describe the degree of differentiation of prostate cancer cells. The Gleason system uses scores ranging from Grade 2 to Grade 10. Lower Gleason scores describe well-differentiated, less aggressive tumors. Higher scores describe poorly differentiated, more aggressive tumors. Other grading systems include, for example, the Bloom-Richardson system for breast cancer and the Fuhrman system for kidney cancer.

In some embodiments, a tumor is evaluated by FACT measurement and a presence and/or high level of FACT is indicative of a higher grade cancer. In these embodiments, a patient suffers from an aggressive cancer and an aggressive treatment regime is employed, including the treatments described herein, such as adjuvant and neoadjuvant therapies. Alternatively, these circumstances may direct cessation of aggressive treatment and the use of palliative care, to avoid unnecessary toxicity from ineffective chemotherapies for a better quality of life.

Conversely, in some embodiments, a tumor is evaluated by FACT measurement and an absence and/or low level of FACT is indicative of a lower grade cancer. In these embodiments, a patient suffers from a less aggressive cancer and a less aggressive treatment regime is employed, including the treatments described herein. In these embodiments, adjuvant and neoadjuvant therapies may be curtailed or avoided altogether.

In various embodiments, aggressive treatment may include a combination of surgery and radiation and chemotherapy, or a combination of surgery and radiation, or a combination of surgery and chemotherapy.

Histological subtypes refer to the use of histology to classify cancer subtypes. For example, in breast cancer, exemplary subtypes are mucinous and tubular. These subtypes are viewed as favorable or less aggressive.

In some embodiments, the present methods replace or augment the use of histological subtypes in directing cancer treatment.

Cancer survival rates or survival statistics may refer to the percentage of people who survive a certain type of cancer for a specific amount of time. Cancer statistics often use an overall five-year survival rate. For example the overall five-year survival rate for bladder cancer is 80 percent, i.e. 80 of every 100 of people diagnosed with bladder cancer were living five years after diagnosis and 20 out of every 100 died within five years of a bladder cancer diagnosis. Other types of survival rates may be used, for example: disease-free survival rate (number of people with cancer who achieve remission) and progression-free survival rate. (number of people who still have cancer, but their disease is not progressing).

In some embodiments, a tumor is evaluated by FACT measurement and a presence and/or high level of FACT is indicative of a lower overall survival probability. In these embodiments, a patient suffers from an aggressive cancer and an aggressive treatment regime is employed, including the treatments described herein such as adjuvant and neoadjuvant therapies. Alternatively, these circumstances may direct cessation of aggressive treatment and the use of palliative care, to avoid unnecessary toxicity from ineffective chemotherapies for a better quality of life.

Conversely, in some embodiments, a tumor is evaluated by FACT measurement and an absence and/or low level of FACT is indicative of a higher overall survival probability. In these embodiments, a patient suffers from a less aggressive cancer and a less aggressive treatment regime is employed, including the treatments described herein. In these embodiments, adjuvant and neoadjuvant therapies may be curtailed or avoided altogether.

Probability of metastasis refers to the likelihood that a cancer will take on metastatic properties.

In some embodiments, a tumor is evaluated by FACT measurement and a presence and/or high level of FACT is indicative of a higher probability of metastasis. In these embodiments, a patient suffers from an aggressive cancer and an aggressive treatment regime is employed, including the treatments described herein such as adjuvant and neoadjuvant therapies. Alternatively, these circumstances may direct cessation of aggressive treatment and the use of palliative care, to avoid unnecessary toxicity from ineffective chemotherapies for a better quality of life.

Conversely, in some embodiments, a tumor is evaluated by FACT measurement and an absence and/or low level of FACT is indicative of a lower probability of metastasis. In these embodiments, a patient suffers from a less aggressive cancer and a less aggressive treatment regime is employed, including the treatments described herein. In these embodiments, adjuvant and neoadjuvant therapies may be curtailed or avoided altogether.

Cancer cell markers refer to properties of cancer or malignancy, including the expression of certain genes/proteins that are indicative of cancer. These markers are known in the art. In some embodiments, certain cancer cell markers are indicative of aggressive cancers, while others are not. For example, in breast cancer: basal, triple negative, ER negative, and Her2 positive are indicative of aggressive cancers. Conversely, luminal, hormone receptor positive, ER positive and Her2 negative are indicative of less aggressive cancers.

For non-small cell lung cancer (NSCLC), undifferentiated large cell carcinoma indicates aggressive cancer, while other types of lung cancer suggest less aggressive cancers. For renal cell carcinoma (RCC), papillary and sarcomotoid carcinomas indicate aggressive cancers while the lack of these carcinomas is indicative of less aggressive cancers.

In some embodiments, a tumor is evaluated by FACT measurement and a presence and/or high level of FACT is indicative of a presence of cancer cell markers associated with aggressive cancers. In these embodiments, a patient suffers from an aggressive cancer and an aggressive treatment regime is employed, including the treatments described herein such as adjuvant and neoadjuvant therapies. Alternatively, these circumstances may direct cessation of aggressive treatment and the use of palliative care, to avoid unnecessary toxicity from ineffective chemotherapies for a better quality of life.

Conversely, in some embodiments, a tumor is evaluated by FACT measurement and an absence and/or low level of FACT is indicative of an absence of cancer cell markers associated with aggressive cancers. In these embodiments, a patient suffers from a less aggressive cancer and a less aggressive treatment regime is employed, including the treatments described herein. In these embodiments, adjuvant and neoadjuvant therapies may be curtailed or avoided altogether.

In some embodiments, the low risk classification is indicative of withholding of neoadjuvant and/or adjuvant therapy. In some embodiments, the low risk classification patient does not receive neoadjuvant and/or adjuvant therapy.

In some embodiments, the high risk classification is indicative of providing neoadjuvant and/or adjuvant therapy. In some embodiments, the high risk classification patient receives neoadjuvant and/or adjuvant therapy.

The invention also provides advantages that may differ depending on the type and stage of the cancer. In some embodiments, the tumor has not invaded the underlying tissue, and the evaluation is useful to prompt a treatment regimen to prevent progression of malignancy and prevent further invasiveness. In these embodiments, the treatment regimen is optionally less aggressive than what would be undertaken in an aggressive cancer. In still other embodiments, the cancer has invaded the underlying tissue, but there is no local lymph node involvement or metastasis and the evaluation is useful to prompt a treatment regimen to prevent progression of malignancy and prevent further invasiveness. In these embodiments, the treatment regimen is optionally more aggressive than what would be undertaken if the tumor has not invaded the underlying tissue. In other embodiments, there is involvement of local lymph nodes, but no metastasis to distant sites and the evaluation is useful to prompt a treatment regimen to prevent progression of malignancy and prevent further invasiveness. In such embodiments, the treatment regimen is optionally very aggressive. Alternatively, the FACT and/or SSRP1 and/or SPT16-based evaluation described herein, in these circumstances, may direct cessation of aggressive treatment and the use of palliative care, to avoid unnecessary toxicity from ineffective chemotherapies for a better quality of life. In still other embodiments, the cancer has multiple metastatic foci and the evaluation is useful to prompt a treatment regimen to prevent progression of malignancy and prevent further invasiveness. In such embodiments, the treatment regimen is optionally very aggressive. Alternatively, the FACT and/or SSRP1 and/or SPT16-based evaluation described herein, in these circumstances, may direct cessation of aggressive treatment and the use of palliative care, to avoid unnecessary toxicity from ineffective chemotherapies for a better quality of life.

The FACT and/or SSRP1 and/or SPT16-based evaluation described herein can be indicative of the stage of the cancer. By way of non-limiting example, using the overall stage grouping, Stage I cancers are localized to one part of the body; Stage II cancers are locally advanced, as are Stage III cancers. Whether a cancer is designated as Stage II or Stage III can depend on the specific type of cancer. In one non-limiting example, Hodgkin's disease, Stage II indicates affected lymph nodes on only one side of the diaphragm, whereas Stage III indicates affected lymph nodes above and below the diaphragm. The specific criteria for Stages II and III therefore differ according to diagnosis. Stage IV cancers have often metastasized, or spread to other organs or throughout the body.

Thus, in some embodiments, the cancer is stage I and is not locally advanced. In accordance with these embodiments, the tumor evaluation described herein may direct less aggressive treatment. In some embodiments, the cancer is stage II or III, that is, the cancer may be locally advanced. In accordance with these embodiments, the tumor evaluation described herein may direct more aggressive treatment. Alternatively, the FACT and/or SSRP1 and/or SPT16-based evaluation described herein, in these circumstances, may direct cessation of aggressive treatment and the use of palliative care, to avoid unnecessary toxicity from ineffective chemotherapies for a better quality of life. In still other embodiments, the cancer is stage IV, or is metastatic. In accordance with these embodiments, the tumor evaluation described herein may direct more aggressive treatment. Alternatively, the FACT and/or SSRP1 and/or SPT16-based evaluation described herein, in these circumstances, may direct cessation of aggressive treatment and the use of palliative care, to avoid unnecessary toxicity from ineffective chemotherapies for a better quality of life.

In some embodiments, the cancer is non-resectable. A non-resectable cancer is a malignancy which cannot be surgically removed, due either to the number of metastatic foci, or because it is in a surgical danger zone. In some embodiments, the evaluation directs treatment which prepares the patient, and/or reduces tumor volume, prior to chemotherapeutic and/or radiation treatment, and may decrease the dose of chemotherapy or radiation required.

In some embodiments, the cancer is multidrug resistant. For example, the patient may have undergone one or more cycles of chemotherapy, without substantial response. Alternatively or in addition, the tumor has one or more markers of multidrug resistance. Such markers can include chemoresponse assays or molecular assays. Thus, as used herein, the term multidrug resistant means that the cancer has exhibited non-responsiveness to at least one cycle of combination chemotherapy, or alternatively, has scored (diagnostically) as resistant to at least two of (including comparable agent to) docetaxel, paclitaxel, doxorubicin, epirubicin, carboplatin, cisplatin, vinblastine, vincristine, oxaliplatin, carmustine, fluorouracil, gemcitabine, cyclophosphamide, ifosfamide, topotecan, erlotinib, etoposide, and mitomycin. In such embodiments, the FACT and/or SSRP1 and/or SPT16-based tumor evaluation may direct aggressive treatment. Alternatively, the FACT and/or SSRP1 and/or SPT16-based evaluation described herein, in these circumstances, may direct cessation of aggressive treatment and the use of palliative care, to avoid unnecessary toxicity from ineffective chemotherapies for a better quality of life.

In some embodiments, the patient is in remission. For patients that achieve remission, the FACT and/or SSRP1 and/or SPT16-based evaluation described herein may direct less aggressive (e.g. treatment to avoid or delay recurrence), or a treatment useful for maintaining remission, or no treatment.

In other embodiments, the cancer is a recurrence following conventional chemotherapy of an initial cancer. Often, recurrent cancer has developed drug resistance, and thus is particularly difficult to treat and often comes with a poor prognosis for survival. In such embodiments, the FACT and/or SSRP1 and/or SPT16-based evaluation described herein can direct aggressive treatment. Alternatively, the FACT and/or SSRP1 and/or SPT16-based evaluation described herein, in these circumstances, may direct cessation of aggressive treatment and the use of palliative care, to avoid unnecessary toxicity from ineffective chemotherapies for a better quality of life.

In other embodiments, the FACT measurement in the human sample is indicative of a patient that has a poor prognosis for survival with conventional therapy. For example, the prognosis may be an expected (e.g., greater than about 50%, or about 60%, or about 70%, or about 80%, or about 90% chance) survival of less than about five years, less than about three years, less than about two years, or less than about one year. The prognosis may be based on the type of cancer, including population response rates of the cancer type to radiotherapy and/or chemotherapy and/or may be based upon a molecular characterization of the tumor cells, including expression levels of not only FACT, but also, for example, VEGF, PDGFRβ, CD31, HER2, PTEN, ERCC1, BRCA1, TOPO2α, Ki-67, P53, TS, ER, PR, or mutations in one or more of EGFR, ALK, KRAS, BRAF, and PI3K. In some embodiments, the presence of or high levels of FACT and/or SSRP1 and/or SPT16 is indicative of a poor prognosis. In these embodiments, the presence of or high levels of FACT and/or SSRP1 and/or SPT16 may direct aggressive treatment. In these embodiments, the presence of or high levels of FACT and/or SSRP1 and/or SPT16 may cause a patient to receive aggressive treatment.

Alternatively, prognosis may be based on, in addition to FACT, a gene expression signature of the cancer that is indicative of chemotherapy resistance, likelihood of cancer recurrence, or a high risk group for survival. Gene expression signatures are becoming increasingly available for predicting tumor response to therapy and/or other classification of tumors for prognosis. Exemplary gene expression signatures are described in PCT/US2012/022594 (colon cancer), U.S. Pat. No. 8,211,643 (NSCLC), U.S. Patent Publication No. 2010-0331210 (breast cancer), U.S. Pat. Nos. 7,056,674, 7,081,340, 7,569,345, and 7,526,387, each of which is hereby incorporated by reference in its entirety.

In embodiments in which the tumor evaluation comprising FACT-measurement indicates a poor prognosis, this may direct a treatment regimen that is very aggressive. Alternatively, the FACT and/or SSRP1 and/or SPT16-based evaluation described herein, in these circumstances, may instead direct cessation of aggressive treatment and the use of palliative care, to avoid unnecessary toxicity from ineffective chemotherapies for a better quality of life.

In some embodiments, the tumor evaluation takes the place of a performance status. Performance status can be quantified using any system and methods for scoring a patient's performance status are known in the art. The measure is often used to determine whether a patient can receive chemotherapy, adjustment of dose adjustment, and to determine intensity of palliative care. There are various scoring systems, including the Karnofsky score and the Zubrod score. Parallel scoring systems include the Global Assessment of Functioning (GAF) score, which has been incorporated as the fifth axis of the Diagnostic and Statistical Manual (DSM) of psychiatry. A major limitation of the use of performance statuses is there subjectivity and therefore the present invention, in some embodiments, solves this problem.

Higher performance status (e.g., at least 80%, or at least 70% using the Karnofsky scoring system) may indicate treatment to prevent progression of the disease state, and enhance the patient's ability to accept chemotherapy and/or radiation treatment. For example, in these embodiments, the patient is ambulatory and capable of self care. In other embodiments, the evaluation is indicative of a patient with a low performance status (e.g., less than 50%, less than 30%, or less than 20% using the Karnofsky scoring system), so as to allow conventional radiotherapy and/or chemotherapy to be tolerated. In these embodiments, the patient is largely confined to bed or chair and is disabled even for self-care.

In one embodiment, the detection and/or high level of FACT in a human tumor specimen (including, for example, a biopsy) or cells cultured therefrom is indicative of a low performance status. In such embodiments, the FACT assay described herein directs the use of very aggressive treatment. Alternatively, the FACT and/or SSRP1 and/or SPT16-based evaluation described herein, in these circumstances, may direct cessation of aggressive treatment and the use of palliative care, to avoid unnecessary toxicity from ineffective chemotherapies for a better quality of life.

In one embodiment, the lack of detection and/or low level of FACT in a human tumor specimen (including, for example, a biopsy) or cells cultured therefrom is indicative of a high performance status. In such embodiments, the FACT assay described herein directs the use of less aggressive treatment, to spare unneeded toxicity.

The Karnofsky score runs from 100 to 0, where 100 is "perfect" health and 0 is death. The score may be employed at intervals of 10, where: 100% is normal, no complaints, no signs of disease; 90% is capable of normal activity, few symptoms or signs of disease, 80% is normal activity with some difficulty, some symptoms or signs; 70% is caring for self, not capable of normal activity or work; 60% is requiring some help, can take care of most personal requirements; 50% requires help often, requires frequent medical care; 40% is disabled, requires special care and help; 30% is severely disabled, hospital admission indicated but no risk of death; 20% is very ill, urgently requiring admission, requires supportive measures or treatment; and 10% is moribund, rapidly progressive fatal disease processes.

The Zubrod scoring system for performance status includes: 0, fully active, able to carry on all pre-disease performance without restriction; 1, restricted in physically strenuous activity but ambulatory and able to carry out work of a light or sedentary nature, e.g., light house work, office work; 2, ambulatory and capable of all self-care but unable to carry out any work activities, up and about more than 50% of waking hours; 3, capable of only limited self-care, confined to bed or chair more than 50% of waking hours; 4, completely disabled, cannot carry on any self-care, totally confined to bed or chair; 5, dead.

In some embodiments, histological samples of tumors are graded according to Elston & Ellis, Histopathology, 1991, 19:403-10, the contents of which are hereby incorporated by reference in their entirety.

In some embodiments, FACT is a surrogate marker for cancer stem cells that can be used in place of known markers for such cells. In some embodiments, FACT is marker for cancer stem cells that may be used in combination with known markers to improve the likelihood of accurate prediction of whether a patient has such a cell.

Cancer stem cells have an ability for self-renewal and multipotency. The cancer stem cell hypothesis states that, although cancer stem cells represent a rare population of cells within a tumor, their high tumorigenic capacity drives tumorigenesis. Cancer stem cells have extensive proliferative capacity; are capable of asymmetric cell division to generate one or more kinds of differentiated progeny with reduced proliferative or developmental potential; and are capable of symmetric cell divisions for self-renewal or self-maintenance. Due to the intrinsic stem cell-like properties of cancer stem cell, cancer stem cell proliferation generates more cancer stem cells, and all the differentiated cell types that compose the bulk of the tumor. Non-cancer stem cells in the tumor have been shown to proliferate at a faster rate than cancer stem cells, but have little tumor-initiating potential. Because cancer stem cells exhibit increased resistance to toxic and chemical insults, this specific subpopulation of cells is believed to underlie resistance to chemotherapy and disease relapse. In fact, the cancer stem cell model posits that all cancer stem cells must be eradicated to eliminate a tumor and prevent its recurrence.

In some embodiments, the classification of the tumor cell type as comprising a cancer stem cell via FACT detection is indicative of a cancer type that displays resistance to conventional chemotherapy. In some embodiments, a patient with a tumor that is classified as comprising a cancer stem cell via FACT detection is provided chemotherapy that is directed to cancer stem cells and/or known to be effective against cancer stem cells. In some embodiments, such chemotherapy that is directed to cancer stem cells and/or known to be effective against cancer stem cells is selected from BBI608, BBI50, agents that bind with high affinity and specificity to the catalytic site of telomerase (e.g. imetelstat (GRN163L)), GRNOPC1, lycolytic inhibitor 3-bromo-2-oxopropionate-1-propyl ester (3-BrOP) (including, for example, under hypoxic conditions), carmustine, metformin, thioridazine, inhibitors of focal adhesion kinase (FAK) (e.g. defactinib (VS-6063)), VS-4718, VS-5584, sabutoclax, antibodies targeting Delta Like Ligand 4 (DLL4) (including, for example, demcizumab), agents directed to the interleukin-3 receptor (IL-3R) (including, for example, SL-401), and combinations thereof. Conversely, the absence of FACT may indicate that a patient does not have cancer stem cells and may warrant the use of conventional chemotherapy that need not be directed to cancer stem cells and/or known to be effective against cancer stem cells.

In some embodiments, the classification of the tumor cell type as comprising a cancer stem cell via FACT detection is indicative of a cancer type that is likely to relapse. In some embodiments, a detection of FACT in a patient that has been treated for a tumor may direct further monitoring post-treatment. For example, conventional post-treatment monitoring often is no more than once ever 3-4 months in the first 1-2 years after remission and once every 6 month in subsequent years. In some embodiments, the detection of FACT may direct increased monitoring, for example, weekly, bi-weekly, monthly, bi-monthly, and so on, using conventional assays for detection of recurring cancer. The amount of monitoring may remain high even after the first 1-2 years after remission, for example, weekly, bi-weekly, monthly, bi-monthly, and so on, using conventional assays for detection of recurring cancer. In some embodiments, the detection of FACT may direct monitoring of, for example, from 1 to 10 times per year, or at least once every other year, using conventional assays for detection of recurring cancer. Conversely, the absence of FACT may indicate that a patient does not have cancer stem cells and may warrant conventional post-treatment monitoring.

In some embodiments, the detection of FACT in a patient that has been treated for a tumor may direct adjuvant of neoadjuvant therapy because of the likelihood of relapse. In some embodiments, the detection of FACT indicates the presence of cancer stem cells and a high likelihood of relapse and, therefore, such patient may receive adjuvant or neoadjuvant therapy as described herein. Conversely, the absence of FACT may indicate the absence of cancer stem cells and warrant to withholding of adjuvant or neoadjuvant therapy.

In some embodiments, the use of FACT to predict the presence of cancer stem cells is used in conjunction with the other uses of FACT for tumor evaluation described herein (e.g. as an indicator of tumor aggressiveness). For instance, FACT$^+$ patients may receive aggressive treatment on account of the likelihood that their tumors are aggressive and but this treatment may be selected to be a chemotherapy that is effective against cancer stem cells. Further, FACT$^+$ may not only receive aggressive treatment but may also be monitored more frequently than usual after successful treatment.

The methods described herein are applicable to a variety of cancers, including solid tumors and leukemias. In various embodiments, the cancer is a soft-tissue sarcoma, squamous cell carcinoma, fibrosarcoma, myosarcoma, osteogenic sarcoma, angiosarcoma, endotheliosarcoma, or epithelial carcinoma. In some embodiments, the tumor histology is a serous adenocarcinoma, an endometroid adenocarcinoma, a mucinous adenocarcinoma, undifferentiated adenocarcinoma, transitional cell adenocarcinoma, or adenocarcinoma. Exemplary cancers include lung cancer, including SCLC and NSCLC, mesothelioma, brain cancer, glioblastoma, head and neck cancer, esophageal cancer, breast cancer, lymphoma, prostate cancer, pancreatic cancer, liver cancer, stomach cancer, kidney cancer, colon or colorectal cancer, ovarian cancer, endometrial cancer, cervical cancer, testicular cancer, and melanoma. In still other embodiments, the cancer is a leukemia, such as chronic myelogenous leukemia (CML) or acute lymphoblastic leukemia (ALL).

In various embodiments, the cancer is a solid tumor. In some embodiments, the tumor is one or more of a primary or recurrent tumor or a metastatic lesion.

In some embodiments, the tumor is any one of breast, prostate, pancreatic, lung, liver, kidney, bladder, colorectal, ovarian, cervical, head and neck, skin, central and peripheral nervous system.

In various embodiments, the FACT and/or SSRP1 and/or SPT16-based evaluation of tumors directs patient treatment. Patients scoring as FACT$^+$ can receive one or more of the following as primary, adjuvant, or neoadjuvant regimes: chemotherapy regimen (including, for example, monotherapy and combination therapies). The chemotherapy may be, for example but is not limited to, paclitaxel, doxorubicin, mithramycin, docetaxel, platinum-based chemotherapeutics (including, but not limited to, cisplatin and carboplatin), mitomycin, methotrexate, fluorouracil, 5-fluorouracil (5-FU), vinorelbine, topotecan, irinotecan, bleomycin, bleomycin hydrorxyurea, mitomycin, actinomycin, topoisomerase I and II inhibitors, anthracylines, cpirubicin, idarubicin, mitoxantrone, valrubicin, ctoposide, teniposide, rubitecan, and derivatives thereof. The chemotherapy may include a taxane and/or an antimetabolite and/or derivatives thereof.

In addition or in the alternative, a patient may receive a chemotherapy selected from an anthracyclin, taxol or taxoid, vinca alkaloid, alkylating agent, intercalating agent, kinase inhibitor, or nitrogen mustard. Non limiting exemplary agents include one or more of a topoisomerase inhibitor (I or II), apoptosis inducer, protease inhibitor, microtubule inhibitor, mitotic inhibitor, an antimetabolite, signal transduction inhibitor, estrogen receptor inhibitor, EGFR inhibitor, Her2 inhibitor, or an aromatase inhibitor.

In addition or in the alternative, a patient may receive a chemotherapeutic agent that includes one or more of daunorubicin, doxorubicin, epirubicin, idarubicin, adriamycin, vincristine, carmustine, cisplatin, 5-fluorouracil, tamoxifen, prodasone, sandostatine, mitomycin C, foscarnet, paclitaxel, docetaxel, gemcitabine, fludarabine, carboplatin, leucovorin, tamoxifen, goserelin, ketoconazole, leuprolide flutamide, vinblastine, vindesine, vinorelbine, camptothecin, topotecan, irinotecan hydrochloride, etoposide, mitoxantrone, teniposide, amsacrine, merbarone, piroxantrone hydrochloride, methotrexate, 6-mercaptopurine, 6-thioguanine, cytarabine (Ara-C), trimetrexate, acivicin, alanosine, pyrazofurin, pentostatin, 5-azacitidine, 5-azacitidine, 5-Aza-5-Aza-2'-deoxycytidine, adenosine arabinoside (Ara-A), cladribine, ftorafur, UFT (combination of uracil and ftorafur), 5-fluoro-2'-deoxyuridine, 5-fluorouridine, 5'-deoxy-5-fluorouridine, hydroxyurea, dihydrolenchiorambucil, tiazofurin, oxaliplatin, melphalan, thiotepa, busulfan, chlorambucil, plicamycin, dacarbazine, ifosfamide phosphate, cyclophosphamide, pipobroman, 4-ipomeanol, dihydrolenperone, spiromustine, geldenamycin, cytochalasins, depsipeptide, 4'-cyano-3-(4-(e.g., ZOLADEX) and 4'-cyano-3-(4-fluorophenylsulphonyl)-2-hydroxy-3-methyl-3'-(trifluorometh-yl)propionanilide.

In some embodiments, a patient may receive one or more of anti-Her2/neu antibodies such as HERCEPTIN, an anti-EGFR antibody such as ERBITUX, a growth factor receptor antibody such as AVASTIN, a small molecule inhibitor such as TARCEVA, IRESSA, or sunitinib), or anti-CD20 such as RITUXAN. In still other embodiments, a patient receives erlotinib, gefitinib, lapatinib, cetuximab, panitumumab, or imatinib.

In some embodiments, the FACT and/or SSRP1 and/or SPT16-based evaluation of tumors described herein may direct patient treatment with a carbazole compounds, such as, for example, those described in International Patent Publication No. WO 2010/042445, the contents of which are hereby incorporated by reference in their entirety. In some embodiments, the carbazole compound is a curaxin, such as, for example, CBLC000, CBLC100, and CBLC137 (see, e.g., Gasparian, et al. Sci. Trans. Med. 3: 95ra74 (2011), the contents of which are hereby incorporated by reference in their entirety).

The FACT and/or SSRP1 and/or SPT16-based evaluation of tumors described herein may direct patient treatment, including radiation therapy. Radiation therapy may be, for example, external beam therapy (EBT) or intensity-modulated radiation therapy (IMRT). EBT delivers a beam of high-energy X rays to the location of the tumor. The beam is generated outside the patient (usually by a linear accelerator) and is targeted at the tumor site. These X rays can destroy the cancer cells and careful treatment planning allows the surrounding normal tissues to be spared. No radioactive sources are placed inside the patient's body. IMRT is an advanced mode of high-precision radiotherapy that utilizes computer-controlled X ray accelerators to deliver precise radiation doses to a malignant tumor or specific areas within the tumor. The radiation dose is designed to conform to the three-dimensional (3-D) shape of the tumor by modulating, or controlling, the intensity of the radiation beam to focus a higher radiation dose to the tumor while minimizing radiation exposure to healthy cells. Brachytherapy can also be employed, which uses sealed radioactive sources implanted into the treatment area which can be either temporary or permanent.

In some embodiments, a high risk patient receives both chemotherapy and radiation therapy.

Doses of the treatments that may result from the presently invented evaluation of tumors are known in the art, for example, by reference to Physicians' Desk Reference, 66th Edition, PDR Network; 2012 Edition (Dec. 27, 2011), the contents of which are incorporated by reference in its entirety. In vitro or in vivo assays may also be employed to help identify optimal dosage ranges. Dose can depend on several factors including the severity of the cancer, the age, weight, and health of the subject, as well pharmacogenomic parameters.

Methods of administration include but are not limited to oral, subcutaneous, intradermal, intramuscular, intraperitoneal, intravenous, intranasal, epidural, sublingual, intranasal, intracerebral, intravaginal, transdermal, rectally, by inhalation, or topically, particularly to the ears, nose, eyes, or skin. The mode of administration can be left to the discretion of the practitioner. The treatment compositions can optionally comprise a suitable amount of a pharmaceutically acceptable excipient so as to provide the form for proper administration to the subject.

In various embodiments, the present invention includes the measurement of a presence, absence, or level of at least one component of FACT. For example, in some embodiments, the invention includes the measurement of SSRP1 and/or SPT16.

In some embodiments, the measurement of SSRP1 and/or SPT16 comprises the use of an agent that specifically binds to one of SSRP1 and SPT16 protein. For example, such an agent may be an antibody.

In some embodiments, the measurement of SSRP1 and/or SPT16 comprises the use of an agent that specifically binds to one of SSRP1 and SPT16 protein nucleic acids. In some embodiments, the agent may be DNA or RNA. In some embodiments, the agent may be a primer or probe.

In some embodiments, the measurement comprises evaluating a presence, absence, or level of a protein. In some embodiments, the measurement comprises the use of an agent that specifically binds to one of SSRP1 and SPT16 protein and the agent may be, for example, an antibody. In various embodiments, the measurement of one or more of SSRP1 and SPT16 protein levels is any of immunohistochemical staining, western blotting, in cell western, immunofluorescent staining, ELISA, and fluorescent activating cell sorting (FACS).

Methods of an the invention may involve contacting an antibody (e.g. against FACT and/or SSRP1 and/or SPT16) with tumor specimen (e.g. biopsy or tissue or body fluid) in order to identify an epitope that is specific to the tissue or body fluid and that is indicative of a state of a cancer (e.g. FACT and/or SSRP1 and/or SPT16).

There are generally two strategies used for detection of epitopes on antigens in body fluids or tissues, direct methods and indirect methods. The direct method comprises a one-step staining, and may involve a labeled antibody (e.g. FITC conjugated antiserum) reacting directly with the antigen in a body fluid or tissue sample. The indirect method comprises an unlabeled primary antibody that reacts with the body fluid or tissue antigen, and a labeled secondary antibody that reacts with the primary antibody. Labels can include radioactive labels, fluorescent labels, hapten labels such as, biotin, or an enzyme such as horse radish peroxidase or alkaline phosphatase. Methods of conducting these assays are well known in the art. See, e.g., Harlow et al. (Antibodies, Cold Spring Harbor Laboratory, NY, 1988), Harlow et al. (Using Antibodies, A Laboratory Manual, Cold Spring Harbor Laboratory, NY, 1999), Virella (Medical Immunology, 6th edition, Informa HealthCare, New York, 2007), and Diamandis et al. (Immunoassays, Academic Press, Inc., New York, 1996). Kits for conducting these assays are commercially available from, for example, Clontech Laboratories, LLC. (Mountain View, Calif.).

In various embodiments, antibodies include whole antibodies and/or any antigen binding fragment (e.g., an antigen-binding portion) and/or single chains of these (e.g. an antibody comprising at least two heavy (H) chains and two light (L) chains inter-connected by disulfide bonds, an Fab fragment, a monovalent fragment consisting of the $V_L$, $V_H$, $C_L$ and CH1 domains; a F(ab)$_2$ fragment, a bivalent fragment including two Fab fragments linked by a disulfide bridge at the hinge region; a Fd fragment consisting of the $V_H$ and CH1 domains; a Fv fragment consisting of the $V_L$ and $V_H$ domains of a single arm of an antibody; and the like). In various embodiments, polyclonal and monoclonal antibodies are useful, as are isolated human or humanized antibodies, or functional fragments thereof.

Standard assays to evaluate the binding ability of the antibodies toward the target of various species are known in the art, including for example, ELISAs, western blots and RIAs. The binding kinetics (e.g., binding affinity) of antibodies also can be assessed by standard assays known in the art, such as by Biacore analysis.

In another embodiment, the measurement comprises evaluating a presence, absence, or level of a nucleic acid.

A person skilled in the art will appreciate that a number of methods can be used to detect or quantify the DNA/RNA levels of FACT and/or SSRP1 and/or SPT16.

Gene expression can be measured using, for example, low-to-mid-plex techniques, including but not limited to reporter gene assays, Northern blot, fluorescent in situ hybridization (FISH), and reverse transcription PCR (RT-PCR). Gene expression can also be measured using, for example, higher-plex techniques, including but not limited, serial analysis of gene expression (SAGE), DNA microarrays. Tiling array, RNA-Seq/whole transcriptome shotgun sequencing (WTSS), high-throughput sequencing, multiplex PCR, multiplex ligation-dependent probe amplification (MLPA), DNA sequencing by ligation, and Luminex/XMAP.

A person skilled in the art will appreciate that a number of methods can be used to detect or quantify the level of RNA products of the biomarkers within a sample, including arrays, such as microarrays, RT-PCR (including quantitative PCR), nuclease protection assays and Northern blot analyses.

In various embodiments, the invention provides measurement of FACT and/or SSRP1 and/or SPT16 which provides information of a presence or absence and this information directs patient treatment.

In other embodiments, the invention provides measurement of FACT and/or SSRP1 and/or SPT16 to determine a quantitative amount of FACT and/or SSRP1 and/or SPT16. In some embodiments, the invention provides quantifying a number of malignant/tumor cells and determining the percentage of those cells that express FACT and/or SSRP1 and/or SPT16. In some embodiments, a high level of FACT and/or SSRP1 and/or SPT16 is indicative of an aggressive cancer while a low level of FACT and/or SSRP1 and/or SPT16 is indicative of a less aggressive cancer.

In some embodiments, a scoring system for FACT is used that reflects intensity of staining and proportion of positive tumor cells. Any suitable scoring system can be used, including threshold values and continuous scoring systems. For example, the scoring system can use a scale of from 0 to at least 4. In some embodiments, different FACT score cut-offs are: (i) high FACT and/or SSRP1 and/or SPT16 SSRP1 level samples (e.g. indices>4) versus low and negative samples (e.g. indices≤4); (ii) positive FACT and/or SSRP1 and/or SPT16 (e.g. indices>1) and weak/negative (e.g. indices≤1); and (iii) completely negative samples (e.g. indices=0, no detectable FACT and/or SSRP1 and/or SPT16 positive cells) versus all positive samples (e.g. indices>0, any proportion of FACT and/or SSRP1 and/or SPT16 positive cells, including very weak or less than, e.g., 10%).

In some embodiments, a correlation of survival and FACT and/or SSRP1 and/or SPT16 level is obtained and positive and negative FACT and/or SSRP1 and/or SPT16 samples are compared.

As used herein FACT positive refers to a positive detection of FACT or a subunit thereof (e.g. SSRP1 and/or SPT16). In some embodiments, a FACT positive sample includes those in which the number of malignant cells is at least about 5% or at least about 10%. In various embodiments, FACT positive samples include those comprising malignant cells in which greater than about 10%, or about 20%, or about 30%, or about 40%, or about 50%, or about 60%, or about 70%, or about 80%, or about 90%, or about 100%, of malignant cells express FACT and/or SSRP1 and/or SPT16. For example, a FACT threshold for discriminating high or low risk groups is within about 5% to about 50%, such as within about 10% to 30%.

In various embodiments, the present invention provides for a biopsy to be taken from a patient's tumor and, optionally, an identification and/or measurement of malignant cells in the biopsy by, for example a counting of the percent of malignant and, optionally an identification and/or measurement of malignant cells that express FACT and/or SSRP1 and/or SPT16. In some embodiments, the present invention provides for quantification of a percentage of FACT and/or SSRP1 and/or SPT16-expressing malignant cell that allows for the determination of the FACT scoring described herein (and, accordingly, in some embodiments, guides treatment). In some embodiments, scoring of FACT and/or SSRP1 and/or SPT16 establishes the threshold values described herein to determine, for example, disease properties (e.g. tumor aggressiveness). In some embodiments, the measurement of malignant cells may employ the various biomarkers described herein. In some embodiments, the measurement of malignant cells may employ the various experimental techniques described herein.

In various embodiments, the present invention provides for taking a biopsy from a patient's tumor and identifying malignant cells. Individual cells can be identifies using an suitable stain (e.g. using DAPI staining). Malignant cells can be identified by a trained pathologist and/or using tumor/malignancy markers. Malignant portions of the sample are used for evaluating FACT status.

In some embodiments, a determination of the proximity of FACT and/or SSRP1 and/or SPT16 staining may also be performed.

In various embodiments, a control marker is also tested.

In various embodiments, simultaneous or sequential measurement is employed.

In various embodiments, measurements may employ automated or computer-implemented techniques that image a stained tumor sample, and quantify the various markers used, including quantifying cells that express multiple markers. In some embodiments, a pathologist may conduct the measurements described herein.

In various embodiments, automated or computer-implemented technique an/or a pathologist may determine a number or percentage of FACT and/or SSRP1 and/or SPT16 positive cells versus a number or percentage or tumor/malignant cells and calculate a threshold amount or score as described herein.

In various embodiments, the scoring system is coupled with detection assays described herein. For example, in one embodiment, IHC staining of tissue microarrays (TMA) consisting of samples of primary tumor biopsies and where available of matching normal or metastatic lesions is used to evaluate the protein level of FACT and/or SSRP1 and/or SPT16 in human tumor samples.

In some embodiments, measurements of FACT and/or SSRP1 and/or SPT16 are performed on a computer. Accordingly, in some embodiments, the invention provides computer programs and computer implemented products for carrying out the methods described herein. In one embodiment, the application provides a computer program product for use in conjunction with a computer having a processor and a memory connected to the processor, the computer program product comprising a computer readable storage medium having a computer mechanism encoded thereon, wherein the computer program mechanism may be loaded into the memory of the computer and cause the computer to carry out the methods described herein. In another embodiment, the application provides a computer implemented product for predicting a prognosis or classifying a subject by analysis of FACT and/or SSRP1 and/or SPT16 data. Such a computer implemented product may comprise a means for receiving values corresponding to a subject expression profile in a subject sample (e.g. of FACT and/or SSRP1 and/or SPT16) and a database comprising reference data associated with a prognosis, wherein computer implemented product selects the reference data most similar to the subject FACT and/or SSRP1 and/or SPT16 profile, to thereby predict a prognosis or classify the subject.

In some embodiments, the present invention includes an imager to effect detection of a signal that provides measurement.

In various embodiments, an automated device and/or computer may be useful to implement the methods described herein including, for example, steps of imaging, measurement, and/or quantification. In some embodiments, such automated device and/or computer may allow for automation of the measurements described herein.

For example, in one embodiment, the present invention allows for the use of an infrared fluorescence imaging system (e.g. photodynamic eye, Hamamatsu Photonics, Japan, as described in, for example, Kitai, T. et al., Breast Cancer. 2005; 12 (3):211-215, the contents of which are hereby incorporated by reference in their entirety). Such infrared fluorescence imaging systems may comprise of light emitting diodes at, for example, 760 nm as a light source, and a charge coupled device camera cut filter below, for example, 820 nm as a detector.

In another embodiment, the present invention relates to the use of a laser-assisted imaging device (e.g. SPY machine, Novadaq Corp., Bonita Springs, Fla., as described in, for example, Jain, V. et al., International Journal of Surgical Oncology Volume 2013 (2013), Article ID 904214), the contents of which are hereby incorporated by reference in their entirety). Such laser-assisted imaging device may allow for real-time detection of a fluorescent dye.

In another embodiment, the present invention relates to the use of a handheld field-of-view device for the detection of fluorescence (by way of non-limiting example, as described in, Poh, C. F. et al., Clin Cancer Res 2006; 12(22) 2006, the contents of which are hereby incorporated by reference in their entirety). Fluorescence field-of-view devices may comprise of a bench-top light source coupled to a hand-held unit for direct fluorescence visualization. Photographs of tissue fluorescence may be acquired using illumination from the field-of-view device and a digital single lens reflex camera (e.g. Fuji FinePix S2 Pro, Fujifilm, Odawara, Japan) with a long-pass filter (e.g. Schott GG475-3, Howard Glass, Worcester, Mass.). A single lens reflex camera may be equipped with a 105 mm f/2.8 macro lens (e.g. Nikkor-Micro, Nikon, Tokyo, Japan) and a ring flash (e.g. Nikon Macro Speedlight SB-29s, Tokyo, Japan) for white-light images.

In another embodiment, the present invention comprises the use of a fluorescent microscope (e.g. Olympus Microscope, Olympus America, Center Valley, Pa.), as described in, for example, Marcus, A. et al., Am J Clin Pathol 2012; 138 (4) 590-3, the contents of which are hereby incorporated by reference in their entirety.

In another embodiment, the present invention may employ a MDS System (Applied Imaging Corp, Santa Clara, Calif.), as described in, for example, Borgen, E. et al. Cytometry (Communications in Clinical Cytometry) 46:215-221 (2001), the contents of which are hereby incorporated by reference in their entirety. The MDS™ system comprise s of an epifluorescence microscope with computer-controlled stage movements, autofocus mechanism, two filter wheels for the detection of multiple/chromogen/fluorochromes, a black-and-white CCD camera, computer, monitor, and proprietary scanning and analysis software.

In another embodiment, the present invention relates to the use of a portable γ-camera (e.g. Sentinella, S102; Oncovision), as described in, for example, Kitai, T. et al., *Open Surgical Oncology Journal.* 2010, 2, 78-82 and Vermeeren, L. et al., J of Nuclear Medicine 2010; 51(5) 700-703, the contents of which are hereby incorporated by reference in their entirety. The γ-camera system consists of preoperative imaging with a SymbiaT hybrid camera (Siemens) to give SPECT/CT images and use of a hand-held γ-probe (Neoprobe; Johnson & Johnson Medical) along with the γ-camera to give greater sensitivity.

In some embodiments, the present invention includes the measurement of a tumor specimen, including biopsy or surgical specimen samples. In some embodiments, the biopsy is a human biopsy. In various embodiments, the biopsy is any one of a frozen tumor tissue specimen, cultured cells, circulating tumor cells, and a formalin-fixed paraffin-embedded tumor tissue specimen.

In some embodiments, the tumor specimen may be a biopsy sample, such as a frozen tumor tissue (cryosection) specimen. As is known in the art, a cryosection may employ a cryostat, which comprises a microtome inside a freezer. The surgical specimen is placed on a metal tissue disc which is then secured in a chuck and frozen rapidly to about −20° C. to about −30° C. The specimen is embedded in a gel like medium consisting of, for example, poly ethylene glycol and polyvinyl alcohol. The frozen tissue is cut frozen with the microtome portion of the cryostat, and the section is optionally picked up on a glass slide and stained.

In some embodiments, the tumor specimen may be a biopsy sample, such as cultured cells. These cells may be processed using the usual cell culture techniques that are known in the art. These cells may be circulating tumor cells.

In some embodiments, the tumor specimen may be a biopsy sample, such as a formalin-fixed paraffin-embedded (FFPE) tumor tissue specimen. As is known in the art, a biopsy specimen may be placed in a container with formalin (a mixture of water and formaldehyde) or some other fluid to preserve it. The tissue sample may be placed into a mold with hot paraffin wax. The wax cools to form a solid block that protects the tissue. This paraffin wax block with the embedded tissue is placed on a microtome, which cuts very thin slices of the tissue.

In certain embodiments, the tumor specimen contains less than 100 mg of tissue, or in certain embodiments, contains about 50 mg of tissue or less. The tumor specimen (or biopsy) may contain from about 20 mg to about 50 mgs of tissue, such as about 35 mg of tissue.

The tissue may be obtained, for example, as one or more (e.g., 1, 2, 3, 4, or 5) needle biopsies (e.g., using a 14-gauge needle or other suitable size). In some embodiments, the biopsy is a fine-needle aspiration in which a long, thin needle is inserted into a suspicious area and a syringe is used to draw out fluid and cells for analysis. In some embodiments, the biopsy is a core needle biopsy in which a large needle with a cutting tip is used during core needle biopsy to draw a column of tissue out of a suspicious area. In some embodiments, the biopsy is a vacuum-assisted biopsy in which a suction device increases the amount of fluid and cells that is extracted through the needle. In some embodiments, the biopsy is an image-guided biopsy in which a needle biopsy is combined with an imaging procedure, such as, for example, X ray, computerized tomography (CT), magnetic resonance imaging (MRI) or ultrasound. In other embodiments, the sample may be obtained via a device such as the MAMMOTOME® biopsy system, which is a laser guided, vacuum-assisted biopsy system for breast biopsy.

In some embodiments, cohesive multicellular particulates (explants) are prepared from a patient's tissue sample (e.g., a biopsy sample or surgical specimen) using mechanical fragmentation. This mechanical fragmentation of the explant may take place in a medium substantially free of enzymes that are capable of digesting the explant. Some enzymatic digestion may take place in certain embodiments. Generally, the tissue sample may be systematically minced using two sterile scalpels in a scissor-like motion, or mechanically equivalent manual or automated opposing incisor blades. This cross-cutting motion creates smooth cut edges on the resulting tissue multicellular particulates. The tumor particulates each measure from about 0.25 to about 1.5 $mm^3$, for example, about 1 $mm^3$. Subsequent to mincing, the particles may be plated in culture flasks. The number of explants plated per flask may vary, for example, between about one and about 25, such as from about 5 to about 20 explants per flask. For purposes of illustration, the explants may be evenly distributed across the bottom surface of the flask, followed by initial inversion for about 10 to about 15 minutes. The flask may then be placed in a non-inverted position in a 37° C. $CO_2$ incubator for about 5 to about 10 minutes. Flasks are checked regularly for growth and contamination. Over a period of a few weeks a cell monolayer will form. Further, it is believed (without any intention of being bound by the theory) that tumor cells grow out from the multicellular explant prior to stromal cells. Thus, by initially maintaining the tissue cells within the explant and removing the explant at a predetermined time (e.g., at about 10 to about 50 percent confluency, or at about 15 to about 25 percent confluency), growth of the tumor cells (as opposed to stromal cells) into a monolayer is facilitated. In certain embodiments, the tumor explant may be agitated to substantially release tumor cells from the tumor explant, and the released cells cultured to produce a cell culture monolayer. The use of this procedure to form a cell culture monolayer helps maximize the growth of representative tumor cells from the tissue sample.

In some embodiments, the present invention relates to identification of individual cells in a sample, and/or determining normal and/or malignant cells in a sample, and/or determining the presence, absence, and/or quantity and/or proximity of FACT and/or its subunits in malignant cells. In some embodiments, such identification is simultaneous or sequential. In some embodiments, such identification comprises a control measurement of one or more tumor/malignancy markers as disclosed herein.

In one embodiment, the present invention relates to the simultaneous detection of individual cells in a sample and detection of one or more tumor/malignancy markers for and detection of the presence, absence, and/or quantity and/or proximity of FACT and/or its subunits to determine a percent of FACT and/or its subunits expression and/or activity. In some embodiments, the percent of malignant cells expressing FACT and/or its subunits directs a treatment or withholding of treatment as described herein. In various embodiments, the present invention comprises a step of quantifying the number of tumor/malignant cells expressing FACT and/or one of its subunits.

In general, the location of individual cell can be detected by various cytogenetic, nucleic acid, protein, or immunochemical analyses. The presence or absence of various cells can be detected by contacting a sample with a ligand capable of specifically binding to or interacting with a marker, the presence or absence of which or an increase or decrease in its level of presence is specifically associated with a tumor and/or malignancy.

In one embodiment, the presence or absence of individual cells can be measured using an antibody (by way of non-limiting example, MSN-1 antibodies, OXA antibodies, OXB antibodies, PTEN antibodies, anti-LeY antibodies, anti-CAGE antibodies, anti-UPAR antibodies, anti-Hepcidin antibodies, and anti-KLK4 antibodies). In another embodiment, the presence or absence of various cells can be measured using a nucleic acid probe capable of specifically hybridizing with a nucleic acid sequence specifically associated with certain cells, e.g., SNPs, mutations, intron-exon splicing arrangements, transcripts of genes associated with certain cells, genetic sequences or genes associated with certain cells, etc. The term "a nucleic acid sequence", "a nucleic acid" or "nucleic acid probe" may refer to any nucleic acid comprising, for example, from about 5 nucleotides to about 10, 20, 30, 40, 50, 60, 70, 80, 90, 100, 150, 200, 250, 300, 400, 500, 600, 700, 800, 900, 1000, or more nucleotides. The terms include: single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

In various embodiments, the cellular detection described herein can employ any reagent suitable for detection purposes. Such a labeling reagent can include, but is not limited to, various enzymes, prosthetic groups, fluorescent labels, chemiluminescent labels, bioluminescent labels, and radioactive labels. Non-limiting examples of suitable enzymes include: horseradish peroxidase, alkaline phosphatase, β-galactosidase, α-glycerophosphate, aspariginase, glucose-6-phosphate dehydrogenase, glucoamylase, glucose oxidase and acetylcholinesterase. Non-limiting examples of suitable prosthetic group complexes include: streptavidin/biotin and avidin/biotin. Non-limiting examples of suitable fluorescent materials include: umbelliferone, fluorescein, fluorescein isothiocyanate, rhodamine, dichlorotriazinylamine fluorescein, dansyl chloride, allophycocyanin, green fluorescent protein, o-phthaldehyde, phycocyanin and phycoerythrin. Examples of chemiluminescent materials include: acridinium salt, imidazole, oxalate ester, theromatic acridinuum ester, luminol and isoluminol. Non-limiting examples of bioluminescent materials include: luciferase, luciferin, and aequorin. Non-limiting examples of suitable radioactive material include: $^{125}I$, $^{131}I$, $^{35}S$, $^{32}P$, and $^{3}H$.

In some embodiments, the tumor/malignancy markers used in the present invention include, but are not limited to, one or more of MYBL2, MKI67, MAD2L1, AURKA, BCL2, BUB1, BIRC5, ESR1, CENPN, CCNB1, ERBB2, MLF1IP, NUDT1, PLK1, RNASE4, GGH, RRM2, CKS2, MCM4, CDKN3, C16orf61, DLG7, H2AFZ, PFKP, KPNA2, GATA3, CENPF, KRT18, KRT5, CCNE2, MELK, CX3CR1, TRIP13, MCM6, CCND1, PDIA4, CENPA, UBE2S, NCF1, CDC25B, PGR, TGFB3, PSMD2, HMMR, XBP1, TROAP, KNTC2, PRAME, BTG2, KRT8, FOXM1, KYNU, NME1, MCM3, NUSAP1, PCTK1, IGFBP5, CDC2, ERBB3, CSE1L, PTTG1, PRC1, BRRN1, UBE2C, MUC1, KIF23, CDK2, PPP2R5C, RARRES3, PIR, CCT4, KIF14, SLPI, TOP2A, BBC3, RHOC, EZH2, HMGB3, GMPS, YIF1A, NP, DKFZp762E1312, MET, FABP5, DCK, CTSC, CCNB2, FLJ21062, VEGF, 1L32, CDC20, TACC2, IGFBP2, IFI30, ID3, GPSM2, TIMP2, CCNE1, EIF4A1, RFC4, CST3, CCNA2, CENPE, SLC25A5, GSTM3, SLC7A5, LETMD1, RPS4X, TFF3, ATAD2, ACADSB, KRT17, YWHAZ, PSMB7, CNKSR1, EXT1, SMC4, MCM2, GATM, DDOST, PEX12, YY1, TFDP1, LMNB2, HPN, POLQ, PCNA, GTSE1, MAPRE1, PLAUR, PTDSS1, LRRC17, FEN1, NDP, ABCD3, SCUBE2, TP53, AURKB, KIFC1, COL3A1, NPY1R, PTPLB, SFRS1O, SDC1, CDCβ, CD24, TCEAL1 C1orf198, FAM64A, CDCA3, MSN, MYO1O, KIF2C, ASPM, TUBA1, VIL2, CYBRD1, CTSL, SFRS7, SESN1, LRP8, CP, KIT, CNAP1, TFRC, PLOD2, CKS1B, DUSP4, NDRG1, SLC35A1, CIS, CCT5, IFITM1, ITPR3, SAT, FABP7, OMD, ADAMTS1, PPP1R12A, PRLR, FKBP1A, SNRPA1, CCNC, SCAP1, SPRR2C, FADS2, CTSL2, TLE3, PDAP1, IER2, ESPL1, CDH1, UBR2, RAB6A, CD44, FBXO5, F3, PTPRT, RAC-GAP1, CCT7, SLC25A1, C4orf18, TXNRD1, SLC3A2, C1βorf35, INSR, S0D2, GABBR1, SNRPB, EIF2C2, IDI1, CEP55, RLN1, PTMA, KIFI1, SHMT2, FAM89B, TPX2, CFB, EXO1, EIF4EBP1, DHFR, HIPK2, SYNCRIP, BRCA1, ZNF43, LMNB1, PBXIP1, F1O, FCGRT, FUT8, RAD21, FRY, LDHA, VASH1, GRB7, ZMYM4, ACTB, CCL18, MTDH, MS4A7, C17orf27, LOC286052, TACC3, MT1X, TK1, CDH3, CDC42BPA, FUT3, GNAZ, YBX1, GPR126, ARPC4, AP2B1, COL6A1, CXCL9, C14orf45, DIAPH3, DNAJC12, LAPTM4B, TUBA3, DTL, ALDH4A1, 0RC6L, ABLIM1, SHCBP1, FGFR1, ER-RFI1, CIRBP, C20orf43, SLC16A1, SPARC, CYP2J2, AP2A2, SLC39A6, F2, SCD, ECT2, QSCN6L1, H3F3B, COL2A1, TBX19, EDN1, OXCT1, RP13-297E16.1, PALM2-AKAP2, HRB, TUBB, CTPS, CAD, CHI3L1, GREM1, ENO1, PLOD1, SORBS1, TSPAN1, STMN1, HIF1A, MMP7, STK3, GOLPH2, MT2A, FOXC1, SRM, COL1A2, GEMIN4, MAPRE2, PGK1, TIMP1, ZBTB4, CRABP1, MAP3K8, TGFB1, C1Oorf11β, C14orf132, TP53INP1, BLM, CD-C25A, MSX2, MMP23B, ADM, CTSF, SFRP4, HMGA1, MRPS6, AP-BA2BP, STRA13, CDCA8, SQLE, ACSS2, FBP1, PSMA7, HTATIP2, PSMD14, HSPB2, APP, TAS2R5, NFIB, TNFAIP2, NAT1, SC4M0L, HNRPAB, TUBG1, PAXIP1, SEC14L1, SATB1, CELSR2, RNASEH2A, TMEM45A, CDKN1A, PTG-S2, ARF1, HDAC2, BCL6, CKAP4, JUNB, NOLA2, APOD, MMP1, EGFR, CCT6A, HDGFRP3, CES2, SMS, DEPDC1B, TSPAN4, BDH2, EEF1A2, S100A8, WISP1, PGAM1, DYNLT1 and/or ADCY3.

In some embodiments, the tumor/malignancy markers used in the present invention include, but are not limited to, one or more of ALK gene rearrangements, Alpha-fetoprotein (AFP), Beta-2-microglobulin (B2M), Beta-human chorionic gonadotropin (Beta-hCG), BCR-ABL fusion gene, BRAF mutation V600E, CA15-3/CA27.29, CA19-9, CA-125, Calcitonin, Carcinoembryonic antigen (CEA), CD20, Chromogranin A (CgA), Chromosomes 3, 7, 17, and 9p21, Cytokeratin fragments 21-1, EGFR mutation analysis, Estrogen receptor (ER)/progesterone receptor (PR), Fibrin/fibrinogen, HE4, HER2/neu, Immunoglobulins, KIT, KRAS mutation analysis, Lactate dehydrogenase, Nuclear matrix protein 22, Prostate-specific antigen (PSA), Thyroglobulin, Urokinase plasminogen activator (uPA) and plasminogen activator inhibitor (PAI-1), 5-Protein signature (Ova1), 21-Gene signature (Oncotype DX), 70-Gene signature (Mammaprint).

In some embodiments, the tumor/malignancy markers used in the present invention include, but are not limited to, one or more of SSX protein family members, e.g., SSX1, SSX4, SSX5 or fragments thereof, MSN-1, OXA, OXB, PTEN, LeY, CAGE, UPAR, Hepcidin, and KLK4. In some embodiments, the tumor/malignancy markers used in the present invention include, but are not limited to, one or more of prostate-specific antigen (PSA), prostate-specific membrane antigen (PMSA), prostate secretory protein (PSP), prostate acid phosphatase (PAP), human glandular kallekrein 2 (HK-2), prostate stem cell antigen (PSCA) and PTI-1. In some embodiments, the tumor/malignancy markers used in the present invention include, but are not limited to, one or more of β-actin, γ-actin, α-tubulin, cytokeratin, cytokeratin 8 (CK 8), cytoskeletal tropomyosin, F-actin capping protein, hsp 27, hsp 60, hsp 70, hsp 90, grp 78 (BIP), gp 96, gluthathione-S-transferase, gluthathione synthetase, superoxide dismutae, thioredoxin peroxidase, PA28α, ubiquitin thiolesterase, triosephosphate isomerase, aldose reductase, enoyl-CoA hydratase, α-enolase, annexin II, IV and V, stathmin, nicotinamide-N-methyltransferase, B23/nucleophosmin and vimentin.

In some embodiments, prior to the assessment for FACT levels, the growth of the cells may be monitored, and data from periodic counting may be used to determine growth rates which may or may not be considered parallel to growth rates of the same cells in vivo in the patient.

The term subject, as used herein unless otherwise defined, is a mammal, e.g., a human. Experimental animals are also included, such as a mouse, rat, guinea pig, dog, cat, horse, cow, pig, or non-human primate, such as a monkey, chimpanzee, or baboon. In one embodiment, the subject is a veterinary patient, including the animals described herein. In one embodiment, the subject is a human. In some embodiments, the human is a pediatric human. In other embodiments, the subject is an adult human, including, for example, an elderly human.

The invention provides kits that can simplify the evaluation of tumor samples. A typical kit of the invention comprises various reagents including, for example, an agent to detect FACT and/or SSRP1 and/or SPT16. A kit may also comprise one or more of reagents for detection, including those useful in various detection methods, such as, for example, ELISA. The kit can further comprise materials necessary for the evaluation, including welled plates, syringes, and the like. The kit can further comprise a label or printed instructions instructing the use of described reagents.

This invention is further illustrated by the following non-limiting examples.

EXAMPLES

Then methods employed herein are known in the art. Details of some of these methods are provided below.

Reagents: CBLC137 was provided by Cleveland BioLabs, Inc (Buffalo, N.Y.).

Cells: HT1080, WI-38, MCF7 and MCF10A cells were obtained from ATCC. HT1080, WI-38, MCF7 were maintained in DMEM supplemented with 10% heat inactivated (HI) FBS and antibiotics. MCF10A cells were maintained in 1:1 DMEM/F12 supplemented with 5% horse serum, 20 ng/mL EGF, 500 ng/mL hydrocortisone), 0.01 mg/mL insulin, 100 ng/mL cholera toxin and antibiotics. RCC45 and NKE-hTERT cells were already described (Gurova, et al. (2004). Cancer Res 64, 1951-1958). Human mammary epithelial cells were obtained from breast reduction mammoplasty and modified and maintained as is known in the art. Wild type and p53 Knockout Mouse Embryonic Fibroblast (MEF) cells were obtained from 13.5-days pregnant C57/B6 wild type or $p53^{-/-}$ mice and maintained in DMEM with 10% FBS and antibiotics.

Plasmids, Transfection and Lentiviral Transduction: pLV-H-Ras$^{r12}$-Bleo or pLV-Bleo lentiviral vectors were kindly provided by Dr. Andrei Gudkov (Roswell Park Cancer Institute, Buffalo, N.Y.). Human SSRP1 cDNA was cloned into a pLV neo lentiviral vector and verified by sequencing. SUPT16 cDNA was synthesized (Invitrogen, GeneArt AG) using a sequence that had been optimized by DAPCEL, Inc. (Cleveland, Ohio) following DAPCEL, Inc proprietary synonymous codon optimization strategy for enhanced protein expression in homologous and heterologous hosts. The cDNA was cloned into pMLV HygroR lentiviral vector as XbaI-BamHI fragment. Mission® shRNA to SSRP1, Spt16, or GFP was obtained from Sigma-Aldrich Co., (St. Louis, Mo.).

siRNA to SSRP1 (On-Target plus SMART pool, cat# L-011783-00) SPT16 (On-Target plus SMART pool, cat# L-009517-00) and siCONTROL non-targeting siRNA (cat# D-001210-01) were purchased from Thermo Scientific Dharmacon. Transfection was performed using Lipofectamine 2000 reagent (Invitrogen) according to manufacturer protocol. Lentivirus packaging and infection was performed as is known in the art.

Western blotting, fluorescent activated cell cytometry and Immunofluorescent protocols are known in the art.

Replication and transcription rates in cells were measured using EDU and EU kits (Invitrogen) according to manufacturer protocols.

Quantitative RT-PCR: Total RNA was isolated by TRIzol reagent (Ambion) according to the manufacturer's protocol. First-strand cDNA was synthesized from 2 g total RNA using an iScript cDNA Synthesis kit (BioRad) according to the manufacturer's protocol. Quantitative real-time PCR was performed with primers purchased from Applied Biosystems: SSRP1-Hs00172629_m1, SUPT16H-Hs00200446_m1, and 18S-Hs99999901_s1. qPCR was performed with TaqMan gene Expression Master Mix (Applied Biosystems) using the default parameters of the 7900HT sequence detection system (ABI PRISM; Applied Biosystems). To compare gene expressions between samples, the threshold cycle (CT) value was normalized using the mean CT for the reference gene, 18S ribosomal RNA (rRNA). The normalized mRNA level was defined as ACT=CT (test gene)–CT (mean for the reference gene). The final data were expressed as the fold difference between the test sample and the control sample, which was defined as $2^{(\Delta CT\ test - \Delta CT\ control)}$. All reactions were performed in triplicate, and the experiments were repeated at least twice. The results are presented as the mean of at least two experiments.

TMA and patient population: SSRP1 protein expression in cancer patients was assessed using 16 cancer cohorts on TMAs. The TMA contained one tissue core from non-selected, formalin-fixed and paraffin-embedded specimens diagnosed between 1994 and 2002 at the Roswell Park Cancer Institute. Buffalo, N.Y. Patients' age ranged from 25 to 82 years with a median age of 56 years. An experienced surgical pathologist (C.M.) evaluated H&E-stained slides of all specimens prior to construction of the TMA in order to identify representative tumor areas. Histologically, all tumors were graded according to Elston & Ellis, Histopathology, 1991, 19:403-10, the contents of which are hereby incorporated by reference in their entirety. Clinical follow-up data, provided by the Pathology Resource Network or RPCI were available for all cancer patients with a median follow-up period of months (range 0-148 months). All patients included in this study gave informed consent for further analysis of their tissue for research purposes and publication of the data. The Instructional Review Board of RPCI approved the protocol.

TABLE 1A

Description of patients cohorts used for TMAs used in the study

| Cancer Type | TMA ID | Description | Age (Median/Range) | # Patients |
|---|---|---|---|---|
| Breast Cancer | BrCa25 | Stage 1 breast cancer, invasive ductal tumor, ER Positive, Her 2 Negative. 58 patients × 3 cores tumor each, 220 total cores, 174 breast cores, 46 normal-non matching cores. | | 58 |
| Breast Cancer | BrCa38 | All cases included have tumor and matching metastatic lymph node cores included. 45 patients × 6 cores tumor each. 330 total cores, 270 breast cores, 60 normal-non matching cores. 3 tumor cores and 3 metastatic cores were taken per case | | 45 |
| Colon Cancer | GICa3 | Colorectal tumor and normal tissues. 144 Total Cores, 114 Total Colorectal Cores, 90 Tumor Colorectal Cores, 24 Normal Colorectal Cores, 30 Normal Organ Cores. | | |
| Pancreatic Cancer | GICa5 | 7 Patients Included in TMA: 2 Patients had Primary tumor only, 4 Patients had Primary tumor and normal tissue, 1 Patient had Primary, Metastatic, and Normal tissue. These patients had a primary tumor inventory of 1 to 2 cores | | 7 |
| Pancreatic Cancer | GICa6 | 11 Patients Included in TMA: 9 Patients had Primary tumor and normal tissue, 2 Patient had Primary, Metastatic, and Normal tissue. These patients had a primary tumor inventory of 3 and 4 cores | | 11 |
| Pancreatic Cancer | GICa7 | 7 Patients Included in TMA: 5 Patients had Primary tumor and normal tissue, 5 Patients had Primary tumor and normal tissue. These patients had a primary tumor inventory of 5 cores. | | 7 |
| Pancreatic Cancer | GICa8 | 9 Patients Included in TMA: 7 Patients had Primary tumor and normal tissue, 1 Patient had Primary tumor and metastatic tumor, 1 Patient had Primary, Metastatic, and Normal tissue. These patients had a primary tumor inventory of 6 cores | | 9 |
| Pancreatic Cancer | GICa9 | 7 Patients Included in TMA: 7 Patients had Primary tumor and normal tissue | | 7 |
| Pancreatic Cancer | GICa10 | 10 Patients Included in TMA: 8 Patients had Primary tumor and normal tissue. 2 Patients had Primary, metastatic and normal tissue | | 10 |
| Pancreatic Cancer | GICa11 | 12 Patients Included in TMA: 2 Patients had Primary tumor only. 8 Patients had Primary tumor and normal tissue. 2 Patients had Primary, metastatic and normal tissue. | | 12 |
| Pancreatic Cancer | GICa12 | 7 Patients Included in TMA: 5 Patients had Primary tumor and normal tissue, 1 Patient has Primary and metastatic tumor, 1 Patient had Primary, metastatic and normal tissue | | 7 |
| RCC | GUCa2 (Kidney) | Total tumor cases: 120. Total tumor cases with matching normal: 106. Total tumor cases with generic TP normal kidney: 17. Total cores of other normal tissues: 48. Total cores: 288 | | 120 |
| RCC | GUCa3 (Kidney) | Total tumor cases: 117. Total tumor cases with matching normal: 106. Total tumor cases with generic TP normal kidney: 11. Total cores of other normal tissues: 54. Total cores: 288 | | 117 |
| Metastatic RCC | GUCa4 (Kidney) | This TMA contains a total of 75 patients with metastatic renal cell carcimona. 31 of the patients have primary, metastatic, and normal tissue represented; 6 of the patients have primary and metastatic tissue; 38 of the patients have only metastatic tissue represented. This TMA contains 190 total cores. 143 patient cores. 47 normal, nonmatching cores | | 75 |

TABLE 1A-continued

Description of patients cohorts used for TMAs used in the study

| Cancer Type | TMA ID | Description | Age (Median/ Range) | # Patients |
|---|---|---|---|---|
| Stage 1 lung TMA | LUNGCa8 | Total of 76 patients. | | 76 |
| Stage 1 lung TMA | LUNGCa9 | Total of 61 patients | | 61 |

Immunohistochemical staining was done as known in the art.

In Silico Transcriptomics Online—Integrated gene expression reference database (MediSapiens Ltd) is a database software which contains unified mRNA expression data of various healthy and pathological human tissues, with multiple tools for analyzing and visualizing the data. Manually annotated clinical variables have also been included when available, and the tissues have been systematically classified into specifically developed cancer and anatomical groups. The database currently contains 20,064 samples from 251 different studies, of which 15,392 are cancer samples, including 1,227 cancer cell line samples. The data has been collected from publicly available expression databases of which expression data measured on Affymetrix arrays has been included. Data from CEL files of different types of Affymetrix microarray generations has been normalized together in a specifically developed three-step process to create a large integrated data collection across different studies and array generations. This allows comparing samples from distinct sources directly with each other and utilizing them together in meta-analyses, unveiling new possibilities of discoveries unattainable in separate datasets.

The analysis and visualization tools were implemented with the R statistical programming language (R Development Core Team) embedded in a user-friendly graphical user interface. In this study, the dotplot and boxplot tools for overall data visualization across the human transcriptome were used. The dotplot was drawn by plotting the normalized expression values of SSRP1 or SPT16 against tissue definitions as distinct data points, with the plot divided into five segments based on tissues types: healthy tissues, malignant tissues, other diseases, cell lines from healthy tissues, and cancer cell lines; within these segments, anatomical categories of samples are applied. Also descriptive statistics were calculated to distinguish those samples that differ from others within their respective segments, so that a tissue type is singled out and colored on the plot if it has expression levels one standard deviation higher than the average expression of all tissues in the same segment, or the 90th percentile of expression in the tissue is equal or higher than 2 times interquartile range plus the 75th percentile of the same segment. The boxplot for each gene was drawn as a standard box-whisker plot visualizing the gene's expression in healthy and cancer tissues, with the tissue classifications displayed on the X-axis. All tissues with at least five samples were included. The bottom of the box is the 25th percentile of the data, the top of the box is the 75th percentile, and the horizontal line is the median. The whiskers extend to 1.5 times the interquartile range from the edges of the box, and any data points beyond this are considered outliers.

For analyzing the associations between clinicopathological variables and gene expression the expression values of selected in vivo cancer samples against clinical attributes were plotted using the phenoplot tool of IST Online. The phenoplot utilizes predefined subsets of cancer samples from various cancer types, where the samples have been selected based on the availability of relevant clinical variables within the respective cancer types. The phenoplot is a combination of the boxplot and dotplot, so that dots indicate individual samples and box-whisker visualization indicates higher-level distribution of data values. Each group of samples with particular clinical covariate value is shown as a separate segment on the X-axis of the phenoplot. If notches of any two boxes do not overlap vertically it then indicates that medians of the two sample groups differ significantly (with p-value<0.05) from each other's in terms of the expression of the gene in question.

Analysis of TMA: The SSRP1 data was dichotomized. Fisher's exact tests were performed to test the association between the dichotomized SSRP1 expression index and other dichotomized categorical variables such as age ($\geq 60$, <60), or tumor grade (high, low), stage (early late) and expression of disease specific markers where available. Chi-square tests were performed to test for association with categorical variables with more than two levels. Kaplan-Meier survival analyses with logrank tests were employed to assess the correlation between patient survival and SSRP1 expression index. Any test with a p-value<0.05 was considered significant. All statistical analyses were performed using the R statistical programming language.

Example 1: FACT Expression is Elevated Upon In Vitro Transformation

The pattern of expression of FACT subunits during transformation of different normal cells in vitro as well as in human tumor tissues of different types was undertaken.

FACT induction during the process of in vitro transformation was studied by comparing SSRP1 and SPT16 levels between prototype normal cells at different stages of in vitro transformation. Specifically, finite lifespan, immortalized, and transformed cells were studied.

Almost no change of FACT levels between normal human fibroblasts and fibroblasts immortalized with human telomerase, or mouse primary fibroblasts from p53 wild type or knockout animals was observed (FIG. 1A). However, when immortalized fibroblasts were transformed with activated H-RAS$^{V12}$ oncogene, notable increases in FACT levels in both human and mouse cells were observed (FIG. 1B and FIG. 1C). All these fibroblasts (early passage strains, immortalized, or malignantly transformed) cells are not significantly different in proliferation rate and therefore the increase in FACT levels does not reflect expedited cell proliferation.

Figure 2A:
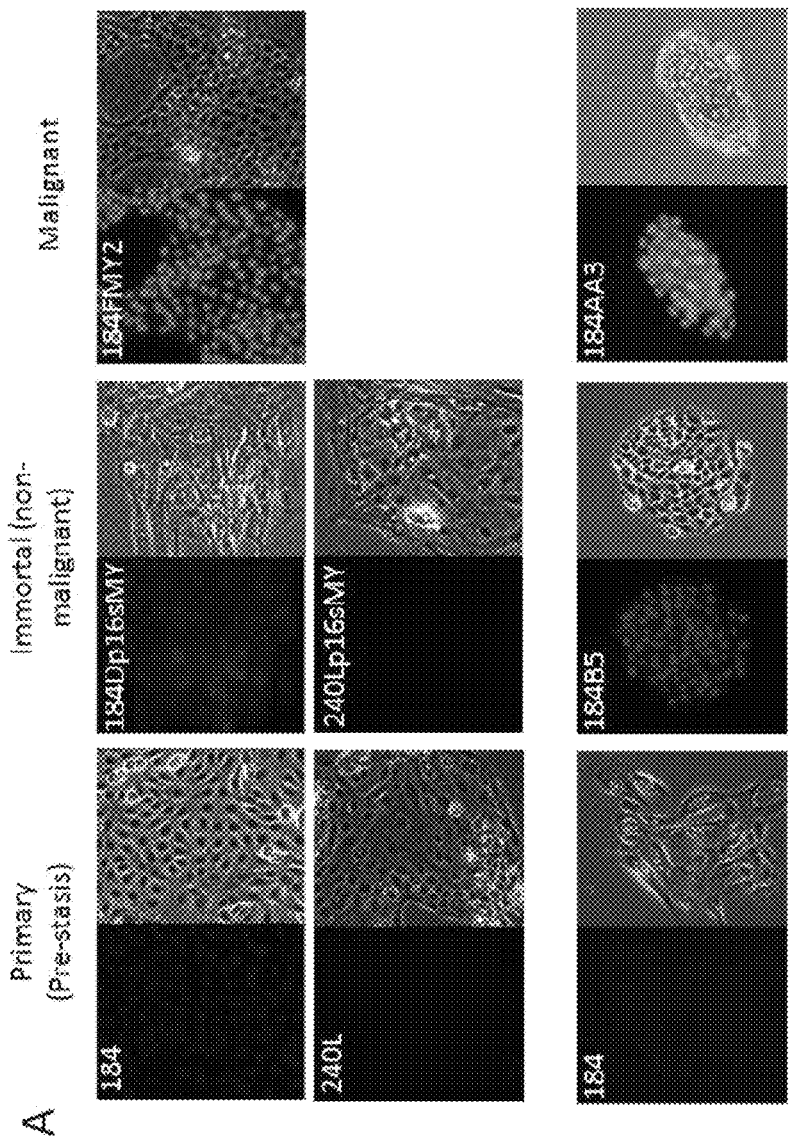
FIGS. 2A, 2B, and 2C show that FACT subunits levels are elevated in the process of transformation of human mammary epithelial cells.
Figure 2B:
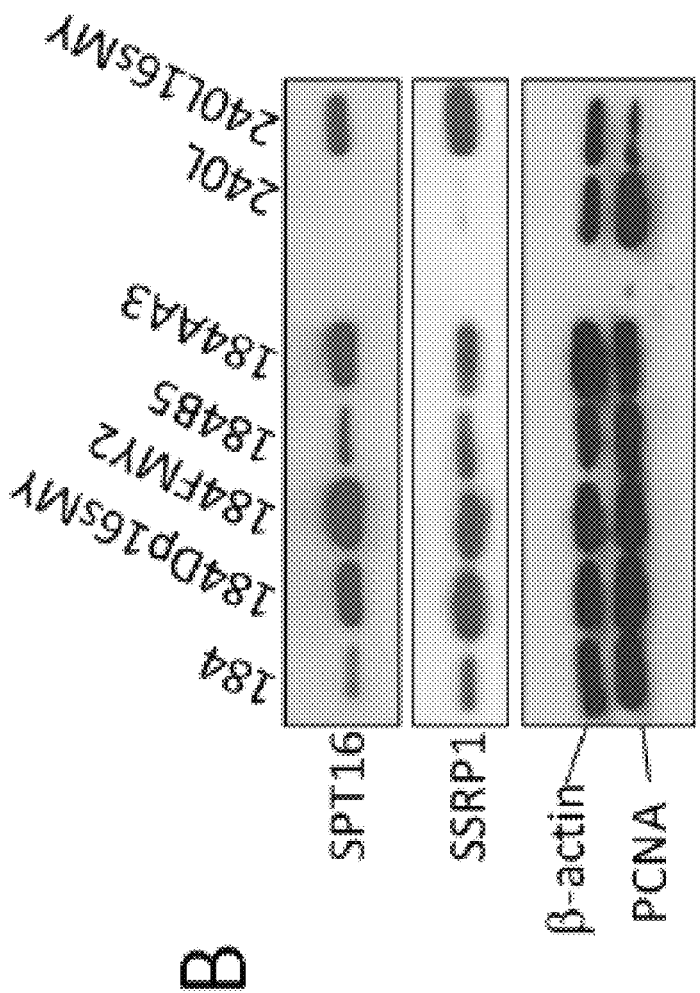
Figure 2C:
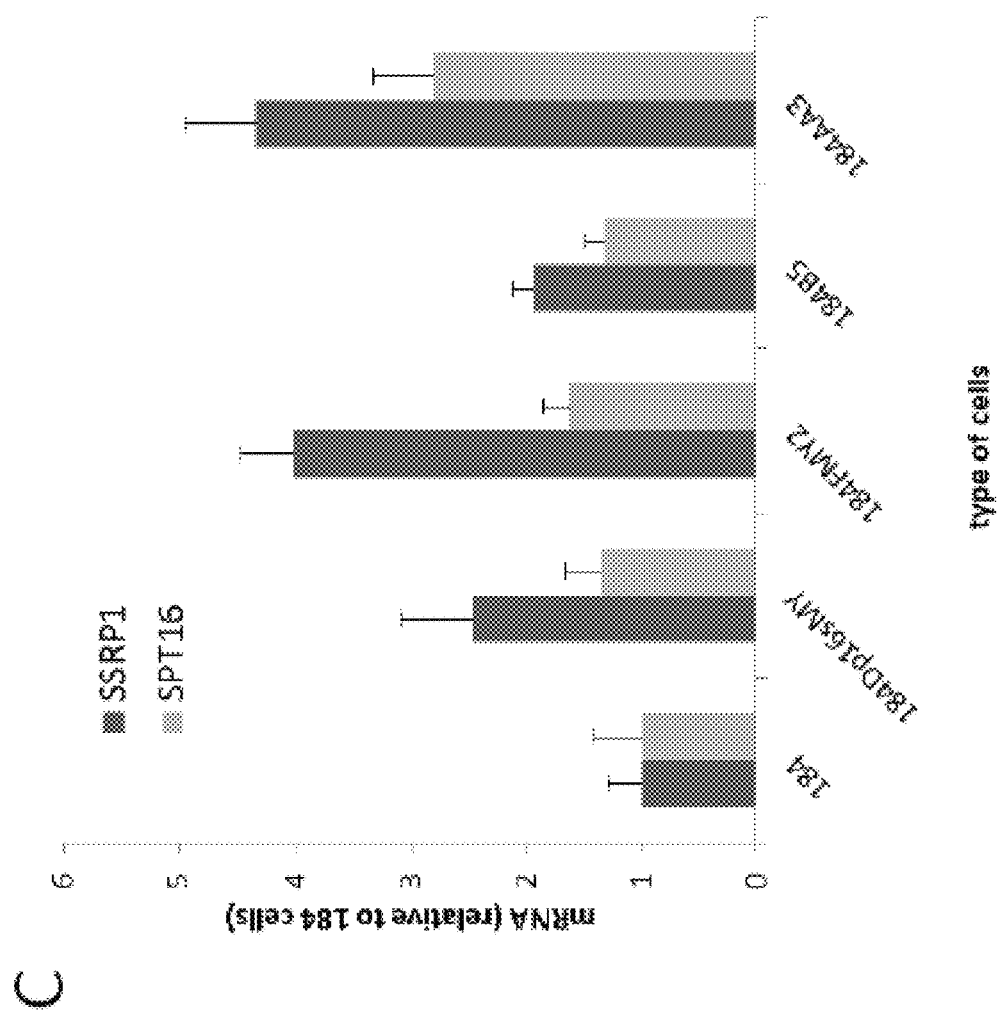

Many human tumors are of epithelial origin. Therefore transformation of epithelial cells in vitro was also undertaken. An isogenic model of mammary epithelial cell transformation as known in the art was utilized. Normal finite-lifespan strains from two reduction mammoplasty specimens, 184 and 240 L, and immortalized lines derived from the normal cells following exposure either to the chemical carcinogen benzo(a)pyrene (184B5, 184AA3) or a set of known genetic constructs that can overcome tumor suppressor barriers (shRNA to CDKN2A (p16) and/or proto-oncogene c-Myc) (184p16sMY, 184FMY2, 240Lp16sMY) were analyzed. The immortalized lines were characterized for anchorage independent growth (AIG) and the ability to form tumors in vivo in immunocompromised mice. 184B5, 184p16sMY, and 240Lp16sMY showed no AIG. Both 184FMY2 and 184AA3 exhibited AIG, but only 184AA3 was tumorigenic. The normal HMEC showed almost no nuclear SSRP1-associated staining, while the highest level of SSRP1 associated immunofluorescence was seen in the lines possessing AIG, 184AA3 and 184FMY2 (FIGS. 2A, 2B, and 2C). The immortalized lines lacking AIG had weak immunofluorescent staining of different intensity (FIG. 2A) but showed significantly increased levels of both SPT16 and SSRP1 compared to normal cells by Western blotting (FIG. 2B). Only SSRP1 mRNA was elevated in transformed HMEC cells somewhat proportionally to its protein level, while SPT16 mRNA was almost unchanged in contrast to SPT16 protein (FIG. 2C). Without wishing to be bound by theory, this may be due to the dependence of SPT16 protein level on SSRP1. Based on PCNA staining, proliferation was not significantly different between these cultures (FIG. 2B).

These experiments demonstrated, inter alia, that transformation of human epithelial cells in vitro is accompanied by elevation of the protein levels of both FACT subunits and that the increase may coincide with acquisition of malignant properties by transformed cells.

Example 2: FACT Subunits are Overexpressed at RNA and Protein Levels in Multiple Samples of Different Types of Tumors Comparison of the mRNA levels of SSRP1 and SPT16 in normal tissues and different tumor was undertaken. High content microarray data of almost all tumor types was examined in these studies. ICT online software (Medisapience, Inc) was used to apply trans-technology and trans-study normalization.

Figure 3A:
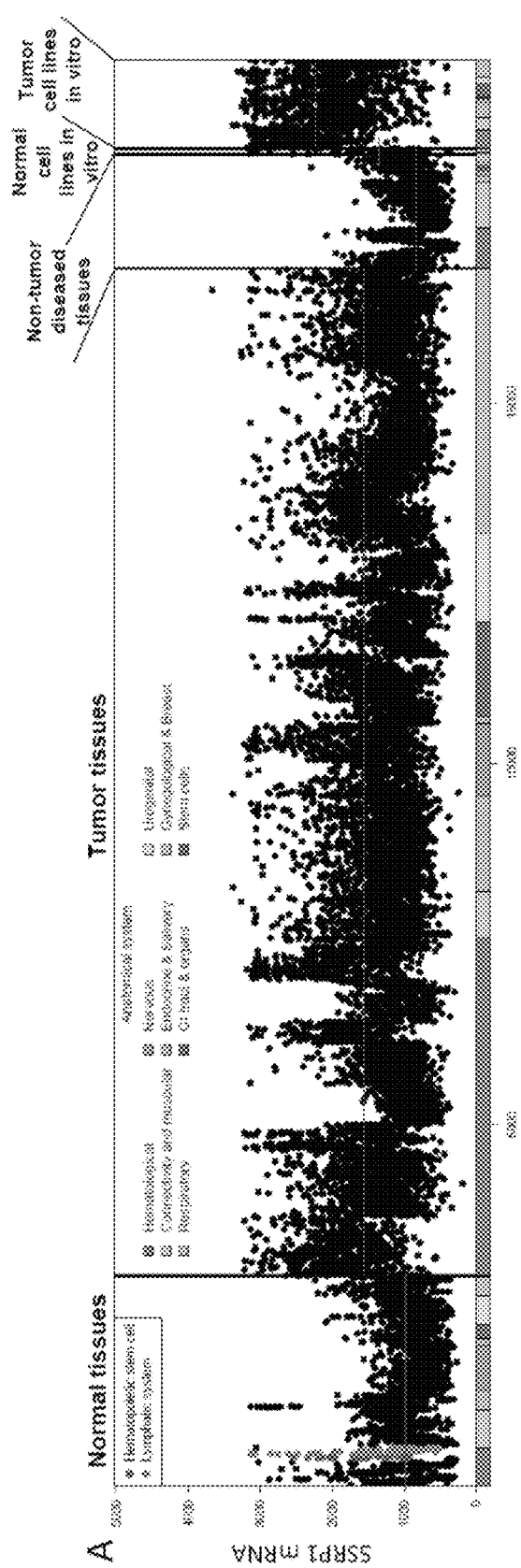
FIGS. 3A and 3B show SSRP1 mRNA expression in different samples.
Figure 3B:
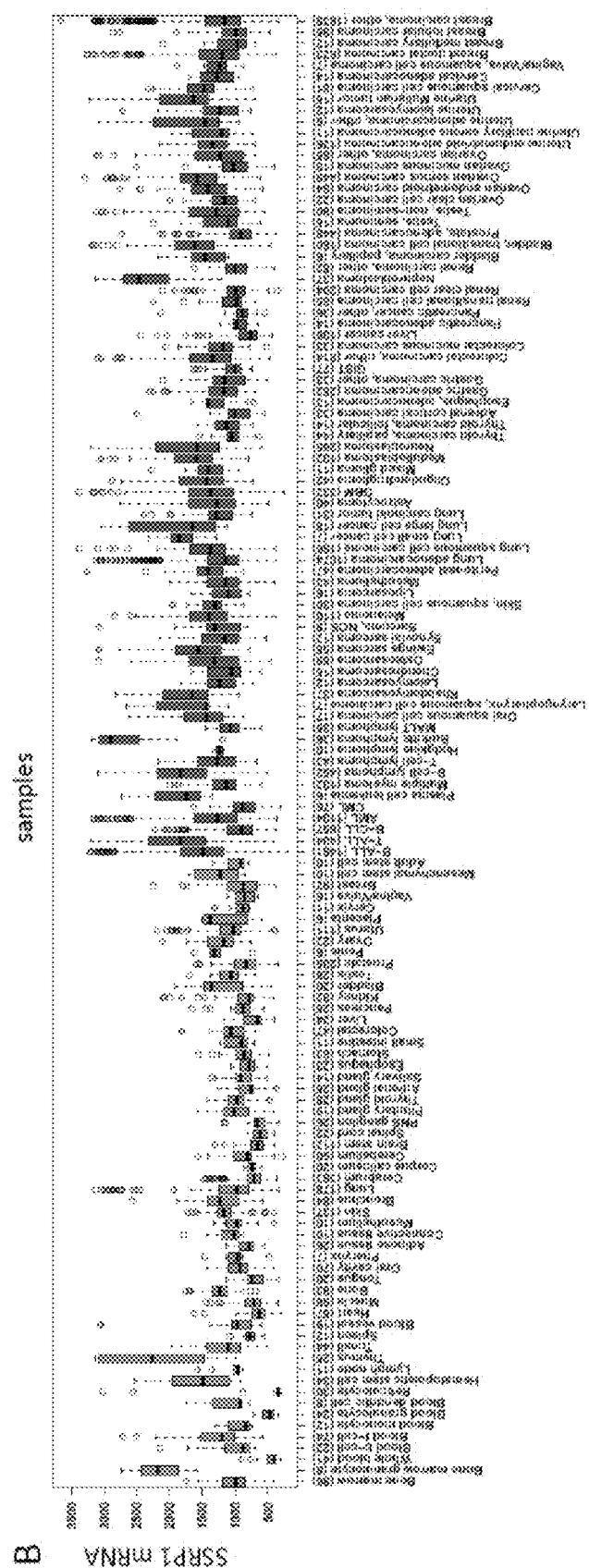

This analysis showed that SSRP1 mRNA is elevated in general in most tumor types compared with healthy normal tissues or tissues from other diseases (FIGS. 3A-3B). However, there are samples with near normal level of SSRP1 mRNA and samples with many fold increase of SSRP1 (FIG. 3A). Also included in this analysis was data from in vitro cell lines which possesses the highest average level of SSRP1 among all categories (FIG. 3A). Without wishing to be bound by theory, this may suggest, for example, that in vitro conditions promote strong elevation of SSRP1 level or only cells with elevated SSRP1 may grow in vitro culture.

Median level of SPT16 mRNA expression in tumor was also elevated, as compared to non-tumor samples, but less substantially than SSRP1. This difference between SSRP1 and SPT16 mRNA data is consistent with the trend observed when a panel of HMEC cells was analyzed (FIGS. 2A-2C). There are significant amount of outliers with very high level of SPT16 mRNA among tumor samples similarly to SSRP1.

IHC staining of tissue microarrays (TMA) consisting of samples of primary tumor biopsies and where available of matching normal or metastatic lesions was used to evaluate the protein level of FACT in human tumor samples. Several groups of TMA consisting of around 854 individual samples from breast, lung, kidney, prostate and several organs of gastro-intestinal tract were employed. Each group was represented by different tumor types proportionally to their incidence in general U.S. population. IHC staining of SSRP1 was used as an indication of the total level of FACT in tumors due to the previously shown high correlation between SSRP1 and SPT16 protein subunits expression in different tissues. This correlation may stem from, without wishing to be bound by theory, the dependence of SPT16 protein level on the amount of SSRP1.

Normal cells of these organs, with the exception of epithelial cells of the bottom of intestinal crypts, do not express SSRP1 protein (FIG. 3A). Therefore, positive SSRP1 staining in tumors of these organs suggests that FACT levels are elevated compared with normal tissues.

Different degrees of SSRP1 overexpression among most of tumor types were observed (FIGS. 4A, 4B, 4C, 4D, 4E). Non-malignant stromal cells were always negative for SSRP1 (FIGS. 4A-4D).

Figures 4A, 4B, 4C, 4D, 4E:
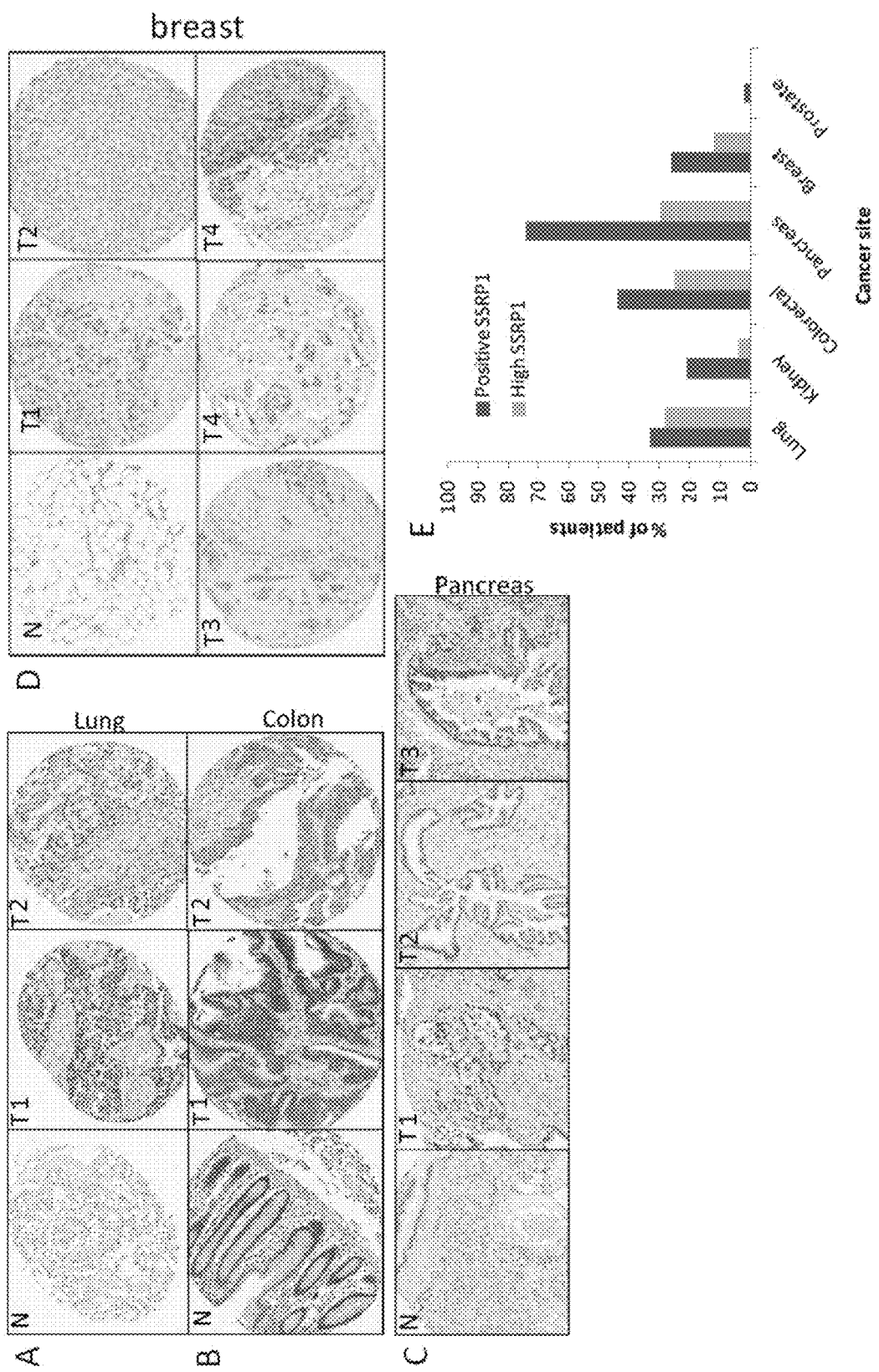
FIGS. 4A, 4B, 4C, 4D, and E show that different types of human tumors express SSRP1 protein. Panels 4A-4D show examples of IHC staining with antibodies to SSRP1 of normal (N) and tumor (T) tissues of various cancers.
FIG. 4E. shows the proportion of samples with SSRP1 expression ("positive"—indices>1, "high" indices>4) from all samples of the same organ analyzed among cancers of different organs.

To consider variability in SSRP1 staining between different samples in the analysis a scoring system that reflects intensity of staining and proportion of positive tumor cells using a scale from 0 to 3 was used. The cumulative SSRP1 index was the product of categorized intensities and proportion scores. "Positive SSRP1" samples with indices>1 include all positive samples, except those where the number of positive cells was less than 10%, or staining was extremely weak (FIG. 4D). "High SSRP1" samples with indices>4 were samples in which most of the tumor cells were highly SSRP1 positive (FIG. 4A, FIG. 3B, FIG. 3D). The highest incidence of SSRP1 positive samples was observed in pancreatic tumors (FIG. 4C and FIG. 4E). There were very few positive SSRP1 samples among prostate cancer patients (FIG. 4E). In contrast to the data obtained on human tumor cell lines in vitro, but in line with RNA expression data, there was certain proportion of tumor samples with no SSRP1 staining among all tumor types (FIG. 4E).

Example 3: Correlation of FACT Subunit Levels and Clinicopathological Features of Tumors The correlation between FACT subunits expressions and clinicopathological features of different types of tumors was examined.

SSRP1 expression between different histological types of cancer within several organs (breast, lung and kidney) where samples were represented by different subtypes were compared.

Figures 5A, 5B, 5C, 5D:
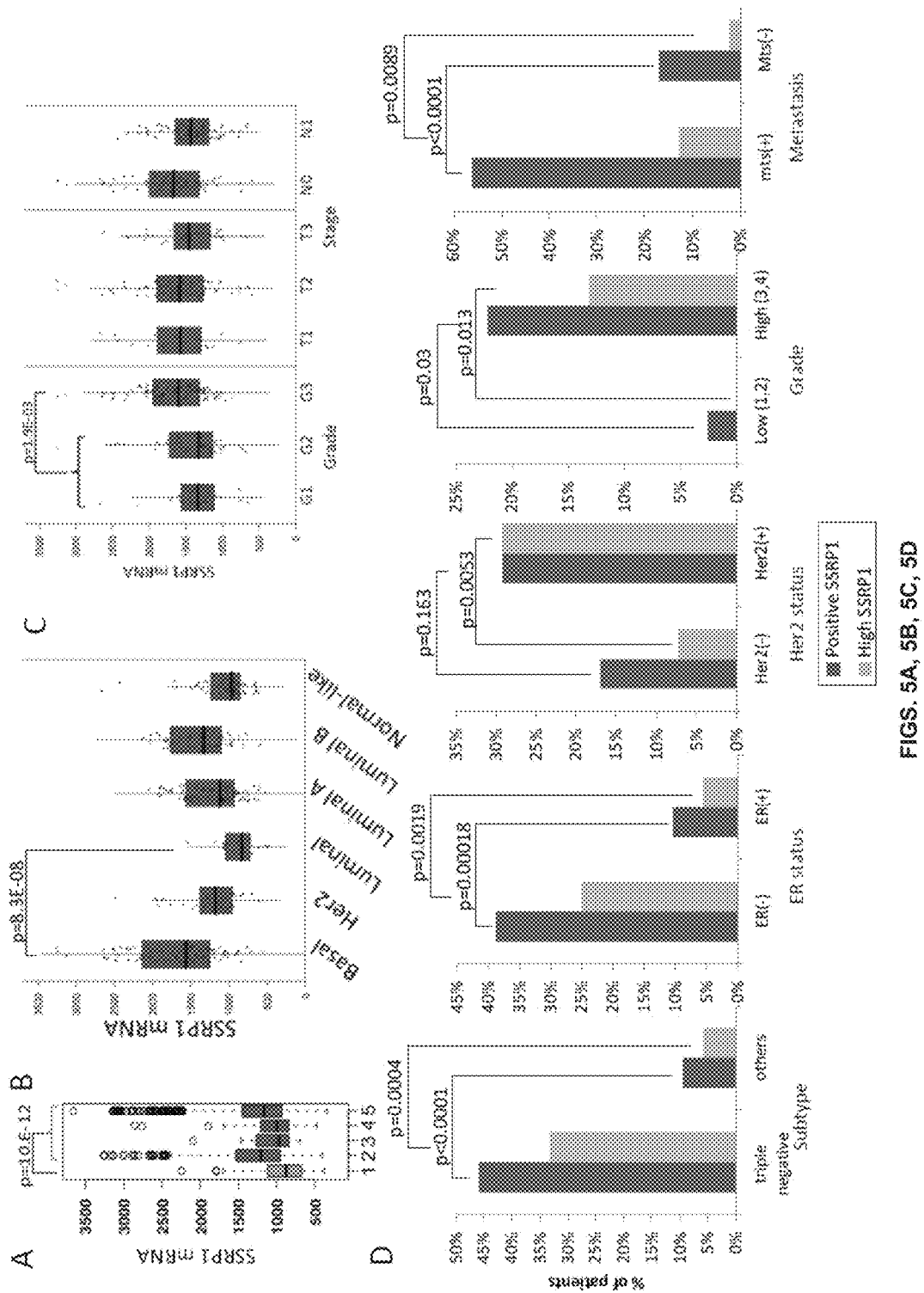
FIGS. 5A, 5B, 5C, 5D show SSRP1 mRNA and protein expression in breast cancer.

Among breast cancer patients, level of SSRP1 mRNA is higher in basal versus luminal carcinoma (FIG. 5A). SSRP1 protein overexpression is more frequent in triple negative versus hormone receptor positive breast carcinomas (Table 1B and FIG. 5B). Also high SSRP1 level correlates with ER negative and Her2 positive status of luminal breast carcinomas (Table 1B and FIG. 5B).

Among non-small cell lung cancer (NSCLC) patients the highest level of SSRP1 mRNA was observed in undifferentiated large cell carcinoma versus other types of lung cancer (Table 1B). The same tendency was observed for SSRP1 protein. Among renal cell carcinoma (RCC) patients, SSRP1 was overexpressed more frequently in samples of papillary and sarcomotoid carcinomas (Table 1B) than others.

All subtypes with higher incidence of SSRP1 positive samples, except papillary RCC, had worse prognosis than corresponding SSRP1 negative subtypes (e.g. in breast cancer: basal versus luminal, triple negative versus hormone receptor positive, ER negative versus positive and Her2 positive versus negative).

Accordingly, SSRP1 positive samples are overrepresented among more aggressive cancer subtypes.

This was confirmed with a correlation analysis between SSRP1 expression and overall survival using TMA staining data. Data using different SSRP1 score cut-offs, (i) high SSRP1 level samples (indices>4) versus low and negative samples (indices≤4); (ii) positive SSRP1 (indices>1) and weak/negative (indices≤1); and (iii) completely negative samples (indices=0, no any SSRP1 positive cells) versus all positive samples (indices>0, any proportion of SSRP1 positive cells, including very weak or less than 10%) were compared.

Figure 6A:
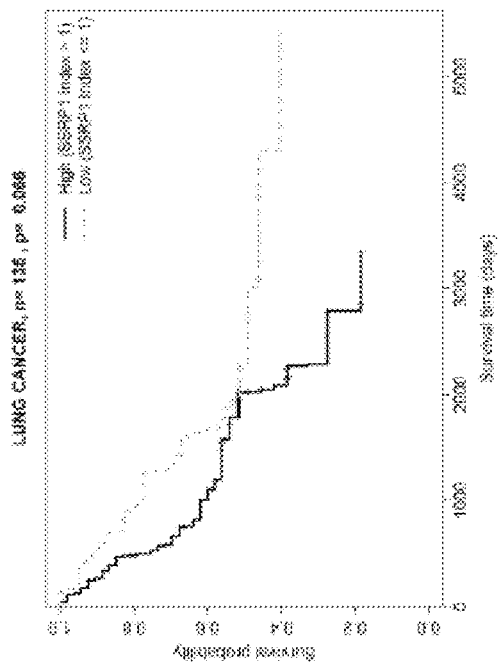
FIGS. 6A-6F show patients with SSRP1 negative tumors have better overall survival. Kaplan-Meier survival curves for all cancer and different cancer sites. P-value was calculated using Long Rank test.
Figure 6B:
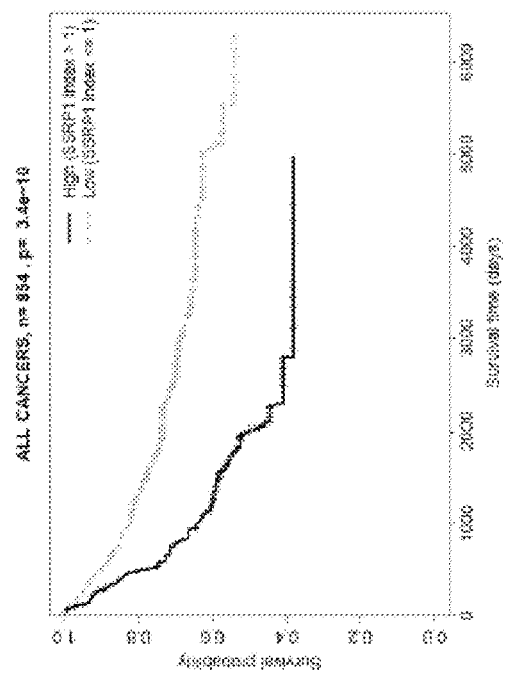
Figure 6C:
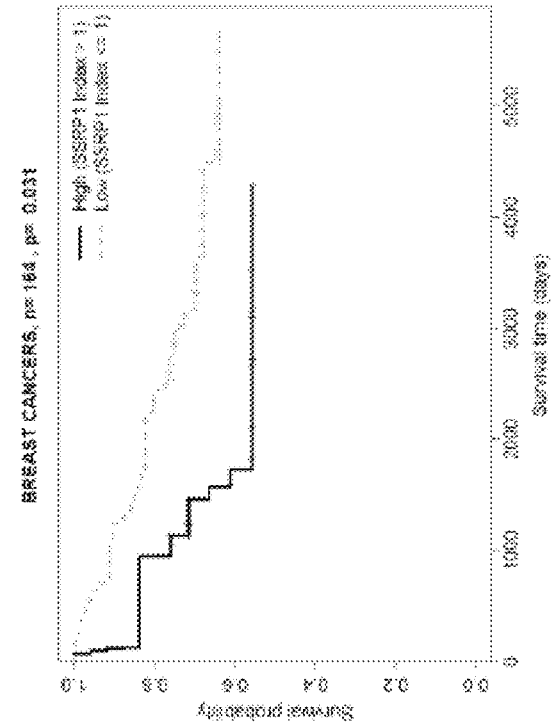
Figure 6D:
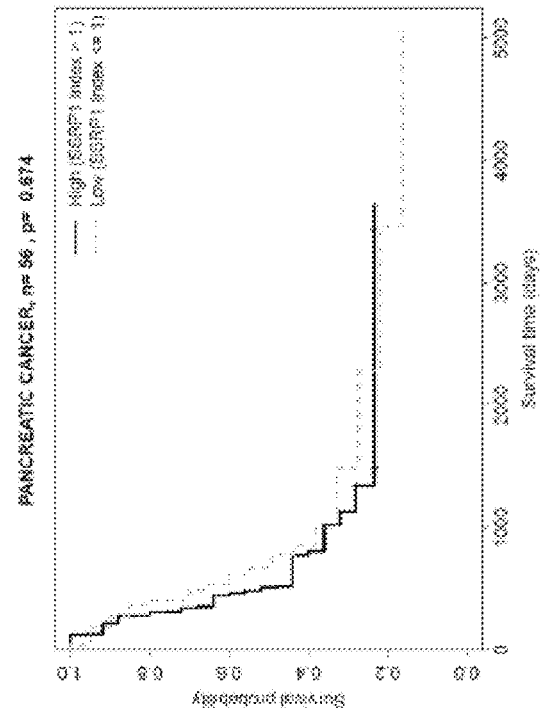
Figure 6E:
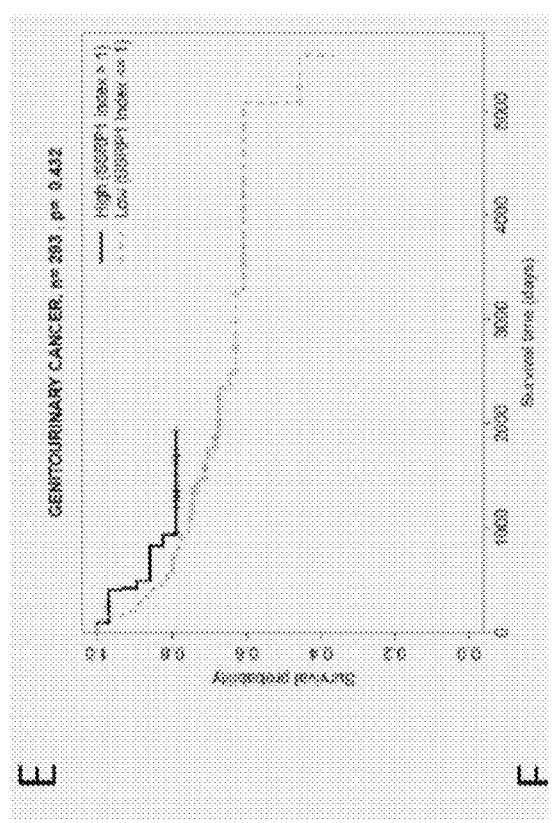
Figure 6F:
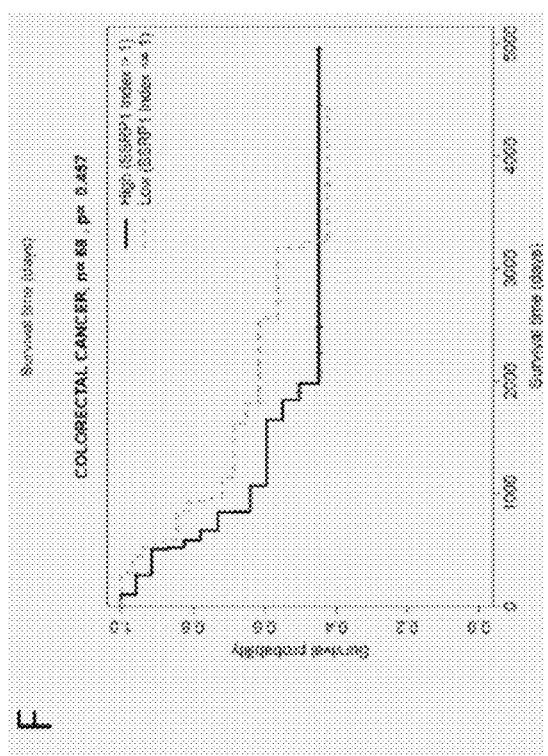

For all tumor types the best correlation of survival and SSRP1 level was obtained if positive and negative SSRP1 samples were compared, as expected based on the comparison of SSRP1 expression in normal and tumor tissue. For all 854 IHC samples, SSRP1 positivity was significantly associated with worse overall survival (FIG. 6A). The same was true when breast cancer was analyzed separately (FIG. 6D).

No correlation between stage of tumor and SSRP1 expression was found in any of tumor type analyzed on protein or mRNA level, suggesting, without wishing to be bound by theory, that expression of FACT subunits does not change with growth of tumor or disease progression (Table 1B). However in several types of cancer, a correlation between tumor grade and FACT subunit level was found (Table 1B). In breast, colon and papillary renal cell carcinomas there were significantly higher levels of SSRP1 mRNA and protein in high grade poorly differentiated tumors (Table 1B, FIG. 5C, FIG. 5D). The same tendency, increase in SSRP1 mRNA and protein with tumor grade, was observed in lung cancer patients and among lung adenocarcinoma stage 2 patients (Table 1B).

It was also shown that patients with breast and renal cell carcinoma, whose primary tumors were SSRP1 positive, have higher incidence of metastatic disease than patients with SSRP1 negative primary tumors (FIG. 5D). SSRP1 mRNA was also higher among patients with metastasis of lung and prostate cancers than among patients with no metastasis. There was high coincidence of SSRP1 status between primary and metastatic lesions in all cancers analyzed by IHC (>87%). Therefore, the presence of SSRP1 in primary tumors of patients with breast, RCC, lung or prostate cancers indicates metastatic disease.

Analysis of SSRP1 expression in clinical samples suggested that SSRP1 is expressed at higher incidence and level in low differentiated (higher grade) and more aggressive tumors such as, (i) subtypes of solid tumors with poor prognosis (breast and lung cancers), (ii) tumors from patients with worse overall survival, (iii) patients with metastatic disease (breast, lung, renal and prostate cancers).

For SPT16, there is high correlation with the expression of SSRP1 in different samples. Without wishing to be bound by theory, SSRP1 and SPT16 are co-regulated in a way that the protein level of one depends on the protein level of the other. For example, there is a strong dependence of SPT16 protein level on SSRP1 mRNA. If tumor cells start expressing a higher level of SSRP1, SPT16 level is also elevated.

Although protein level of SPT16 is elevated in the same tumors in which we saw SSRP1 elevation based on western blotting and IHC, in principle anti-SPT16 antibodies are of much worse quality than SSRP1, therefore we did not use them for TMA stainings.

Example 4: Tumor Cell Survival and Growth is Dependent on FACT Expression

It was examined whether FACT is required for tumor cells or if its overexpression is a marker of some other tumor specific process. It was previously observed that transduction of several tumor cell lines with shRNA to FACT subunits resulted in reduced growth of cells compared with control shRNA. Here the list of cell lines is expanded as well as compared to the effect of shRNA to FACT on tumor and some prototype "normal" cells. The latter is important to know for assessing of a value of targeting FACT for cancer treatment. The present inventors have shown that the level of both FACT subunits are mutually regulated and therefore the use of shRNA against one of the subunits of FACT effectively eliminate both. Several pairs of tumor and non-transformed prototype "normal" cells of the same tissue origin were used, including renal cell carcinoma cells (RCC45) and normal kidney epithelial cells (NKE) immortalized with enzymatic subunit of human telomerase; human fibrosarcoma cells (HT1080) and human diploid fibroblasts (Wi38); and human breast adenocarcinoma cells (MCF7) and immortalized mammary epithelial cells (MCF10A). All used transformed and non-transformed cells express certain level of both FACT subunits in vitro in contrast to normal cells in vivo (compare FIG. 4A-4E and FIGS. 7A-7H).

Figures 7A, 7B, 7C:
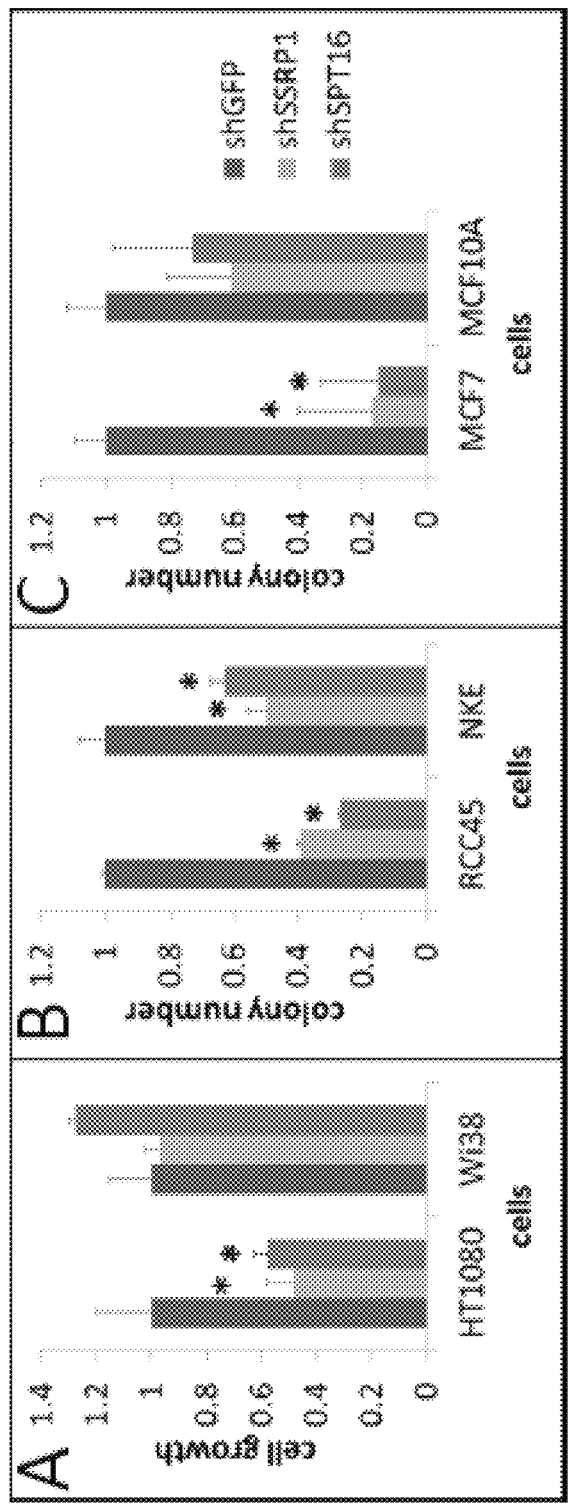
FIGS. 7A-7H shows growth of tumor (HT1080, RCC45, MCF7) and normal (WI38, NKE, MCF10A) cells upon knockdown (KD) of FACT subunits. Methylene blue staining (A) or colony number (B,C) of cells transduced with the indicated lentiviral shRNA and selected at the presence of puromycin. Bars are average numbers relatively to shGFP cells of the same type. Error bars—standard deviation between three replicates within experiment. Asterisk indicates samples significantly different from the corresponding control (p-value<0.05). D-F. Levels of FACT subunits in cells shown on panel A after puromycin selection detected using western blotting. G. Distribution of cells with high and low levels of SSRP1 protein detected using immunofluorescent staining among HT1080 cells 120 and 144 hrs after transduction with shRNA to SSRP1 (upper panels). Three lower panels show DNA content in HT1080 cells transduced with shRNA to GFP or SSRP1. Cells with high and low levels of SSRP1 were analyzed separately. H. EDU incorporation if different cells 3 days after transduction with the indicated lentiviral shRNAs. I. Proportion of dead cells detected using Annexin V and propidium iodide staining (double positive) among HT1080 cells 5 days after transduction with the indicated lentiviral shRNAs.
Figures 7D, 7E, 7F:
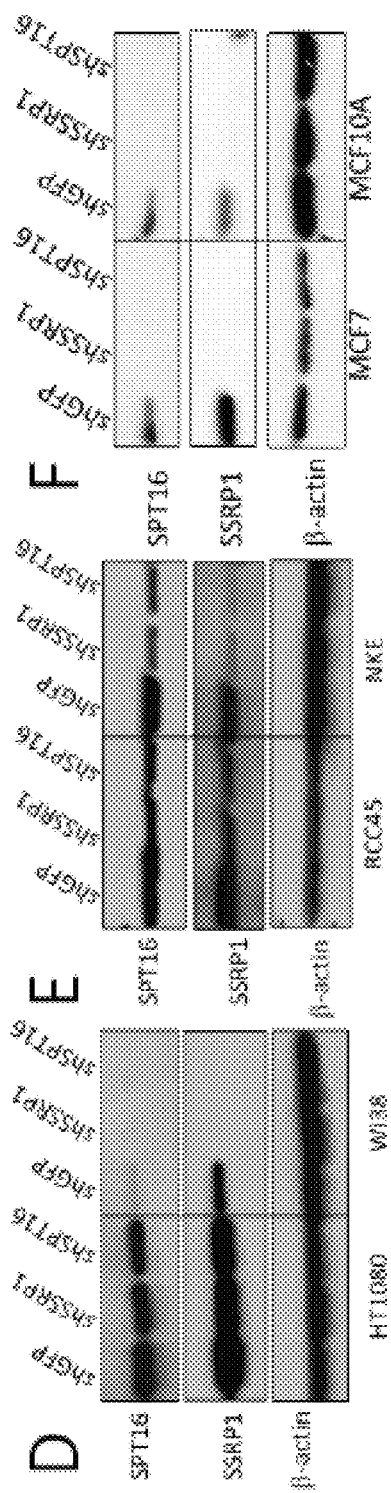

Growth of these cells transduced with shRNAs to FACT subunits or GFP as a control were assessed using colony forming assay (for epithelial cells) or assessing total amount of cells (for fibroblast-like cells, which do not form colonies). Suppression of both FACT subunits expression resulted in reduced growth of all cells except normal fibroblasts, which growth was not affected by any of shRNA used (FIG. 7A-C). Reduction of growth or colony formation was significantly stronger in case of tumor cells than in case of other non-transformed cells (FIG. 7A-C). Analysis of FACT subunits levels in cells that survived shRNA transduction and puromycin selection demonstrated that in two out of three cell pairs (kidney and fibroblasts cells) the SSRP1 and SPT16 KD was very weak in tumor cells while in paired non-transformed cells the reduction was substantial (FIGS. 7D and 7E). Without wishing to be bound by theory, this data suggest that only cells with inefficient KD of FACT may be expanded from tumor cells, while non-tumor cells can grow upon suppression of FACT.

This was tested by measuring levels of FACT subunits and growth of cells at different time points after shRNA transduction using a pair of cells with maximal KD of SSRP1 and SPT16 in tumor cells: MCF7/MCF10A. It was observed that although at the end of puromycin selection there were less MCF10A and MCF7 cells in case of FACT KD as compared to control shGFP cells, after replating, the puromycin-resistant MCF10A were grown independently of the levels of FACT subunits, while in case of MCF7 difference in the growth of cells with lowered level of FACT subunits and control shGFP cells persisted for up to 8 days of observation. Only MCF7 cells with restored level of FACT, started growing similarly to shGFP cells. Moreover while MCF10A cells maintain difference in FACT subunit level for the period of observation, in MCF7 cells this difference was reduced with passaging. Therefore this demonstrated that non-tumor cells with reduced level of FACT grow similarly to control cells while tumor cells did not. Stated otherwise, this experiment demonstrated that tumor cells (MCF7) cannot be propagated upon FACT KD. These cells either do not grow or only those in which KD was inefficient start growing and FACT levels were quickly restored. Conversely, non-tumor cells (MCF10A) can be propagated with reduced level of FACT and these cells can be grown while levels of FACT continue be low.

Figures 7G, 7H:
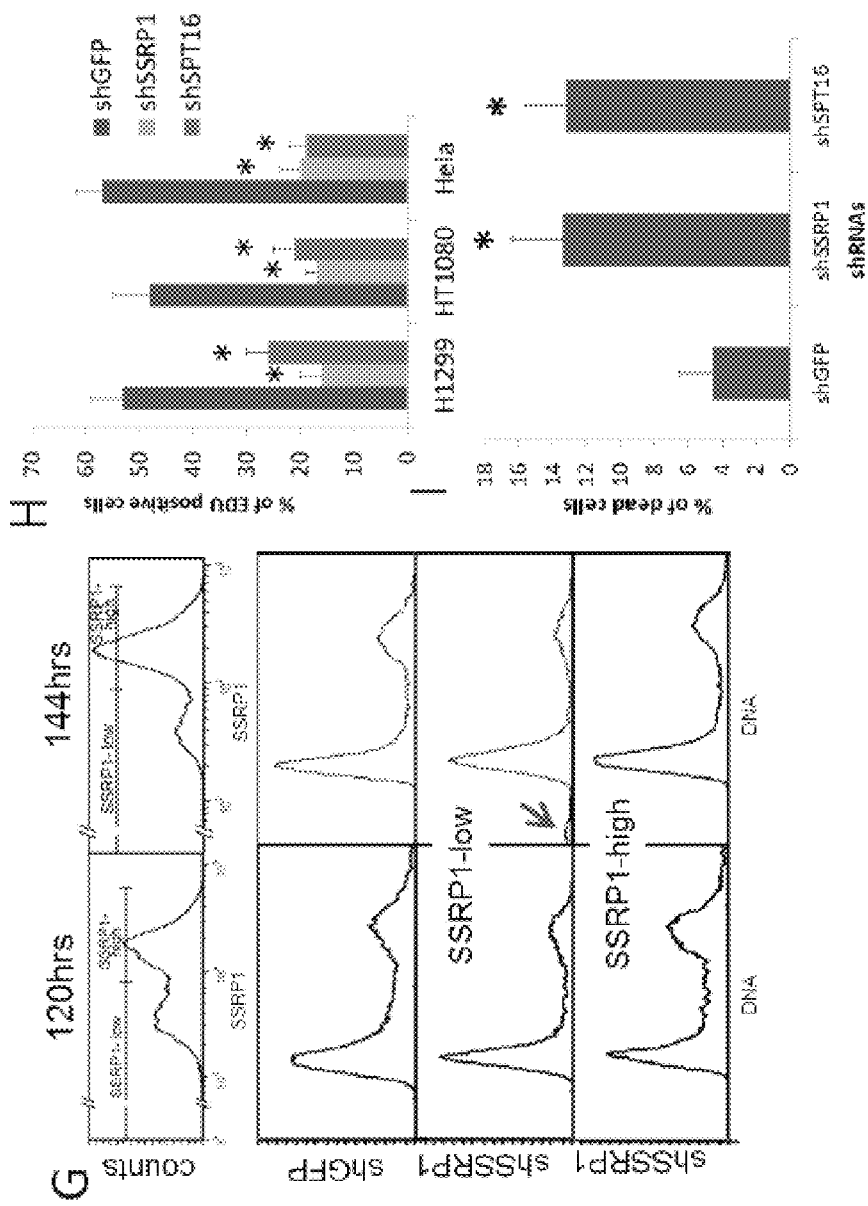

Without wishing to be bound by theory, a potential explanation of why growth of tumor cells is affected by FACT KD was explored. The proportion of cells with low SSRP1 level is reduced with time in shSSRP1 culture (FIG. 7G). Tumor cells with low FACT levels have reduced replication (FIG. 7H) and accumulate in G1 (FIG. 7G); moreover, some of them die (FIG. 7G and FIG. 7I). This data supports the role of FACT in replication. However, absence of S-phase arrest, which is expected if cells lack a factor needed only during replication suggested that certain signaling may exist in cells leading to G1 growth arrest and/or that function of FACT in processes different than replication (i.e. transcription), may be also vital for tumor cells.

Example 5: FACT Subunits as Markers for Cancer Stem Cells

Figure 8A:
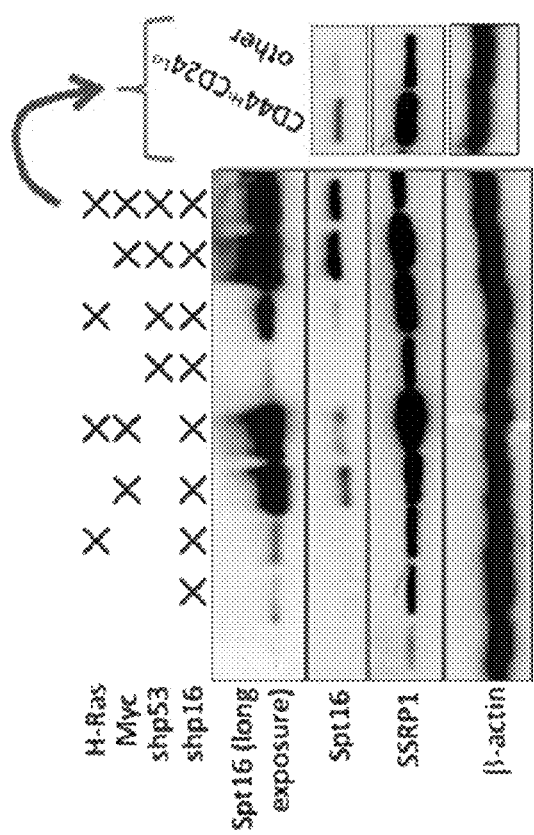
FIG. 8A shows Western blotting of extracts of human mammary epithelial cells for FACT subunits and surface cancer stem cell markers ($CD44^{High}/CD24^{Low}$).
Figure 8B:
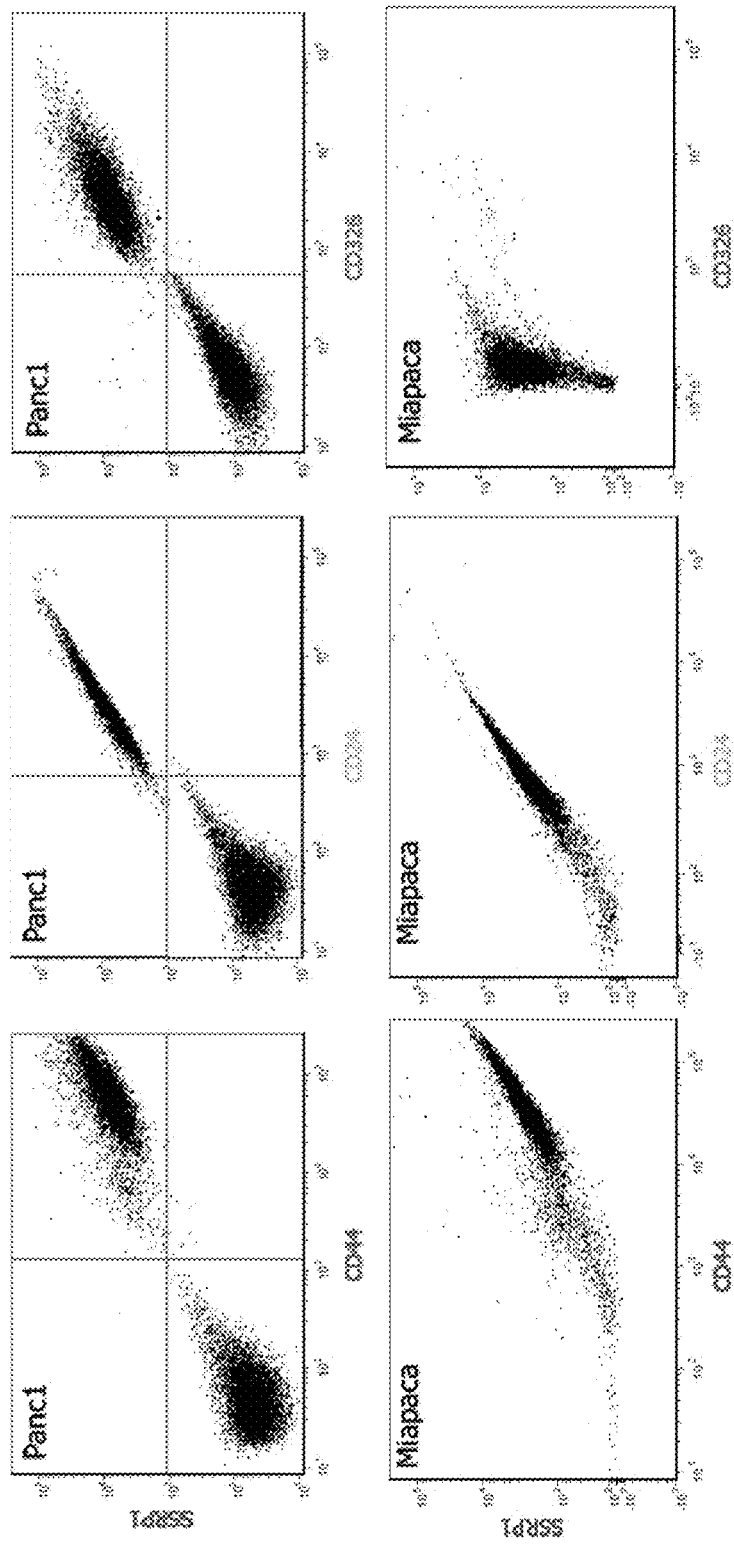
FIG. 8B shows flow cytometry analysis of pancreatic ductal adenocarcinoma cells PANC1 and MIA PaCa costained with antibodies to surface markers present on pancreatic CSC (CD44+/CD24+/CD326+) and SSRP1 subunit of FACT.

Detection of FACT subunits was shown to be useful in identification of cancer stem cells. Both FACT subunits, Spt16 and SSRP1 were found to be expressed at higher levels in in vitro transformed human mammary epithelial cells (HMEC) which express surface cancer stem cell markers ($CD44^{high}/CD24^{Low}$). Western blotting of extracts of HMEC transformed with the indicated genetic constructs is shown in FIG. 8A. Variant of cells transformed upon transduction of all constructs were sorted using flow cytometry based on the detection of antibodies bound to surface CD44 and CD24. The highest level of SSRP1 subunit of FACT was observed in cells with the highest level of expression of pancreatic cancer stem cell surface markers. Flow cytometry analysis of pancreatic ductal adenocarcinoma cells PANC1 and MIA PaCa costained with antibodies to surface markers present on pancreatic CSC (CD44+/CD24+/CD326+) and SSRP1 subunit of FACT is shown in FIG. 8B.

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

INCORPORATION BY REFERENCE

All patents and publications referenced herein are hereby incorporated by reference in their entireties.

What is claimed is:

1. A method for treating a cancerous tumor in a human subject in need thereof, comprising:
   (a) measuring a number of the subject's tumor cells which express SSRP1 and/or SPT16 and the level of SSRP1 and/or SPT16 protein expressed in the subject's tumor cells;
   (b) classifying the subject's tumor as having a high level of cancer aggressiveness or as having a low level of cancer aggressiveness based on a percentage of the subject's tumor cells that express SSRP1 and/or SPT16 and the level of SSRP1 and/or SPT16 protein expressed,
   the classifying comprising using a scoring system that is based upon immunohistochemical staining that reflects intensity of staining and proportion of tumor cells that stain positive for SSRP1 and/or SPT16,
   wherein
   the subject's tumor is characterized as having a high level of cancer aggressiveness when at least 5% or greater of the tumor cells stain positive for SSRP1 and/or SPT16, and
   the subject's tumor is characterized as having a low level of cancer aggressiveness when less than 5% of the tumor cells stain positive for SSRP1 and/or SPT16;
   (c) selecting a therapy for the subject based on whether the subject's tumor has been classified into the high level of cancer aggressiveness or the low level of cancer aggressiveness; and
   (d) administering the selected therapy to the subject.

2. The method of claim 1, wherein the tumor is a primary or a recurrent tumor.

3. The method of claim 1, wherein the measuring comprises one or more of immunohistochemical staining, western blotting, in cell western, immunofluorescent staining, ELISA, and fluorescent activating cell sorting (FACS).

4. The method of claim 1, wherein the tumor specimen is a biopsy selected from a frozen tumor tissue specimen, cultured cells, circulating tumor cells, and a formalin-fixed paraffin-embedded tumor tissue specimen.

5. The method of claim 1, wherein the tumor is any one of breast, prostate, pancreatic, lung, liver, kidney, bladder, colorectal, ovarian, cervical, head and neck, skin, central and peripheral nervous system.

6. The method of claim 1, wherein the high level of cancer aggressiveness is predictive of a positive response to and/or benefit from neoadjuvant chemotherapy.

7. The method of claim 1, wherein the high level of cancer aggressiveness is predictive of a positive response to and/or benefit from adjuvant therapy.

8. The method of claim 1, wherein the high level of cancer aggressiveness is characterizable by one or more of a high tumor grade, low overall survival, high probability of metastasis, and the presence of a tumor marker indicative of aggressiveness.

9. A method for treating a cancerous tumor in a human subject in need thereof, comprising:
   (a) measuring a number of the subject's tumor cells which express SSRP1 and the level of SSRP1 protein expressed in the subject's tumor cells;
   (b) classifying the subject's tumor as having a high level of cancer aggressiveness or as having a low level of cancer aggressiveness based on a percentage of the subject's tumor cells that express SSRP1 and the level of SSRP1 protein expressed, the classifying comprising using a scoring system that is based upon immunohistochemical staining that reflects intensity of staining and proportion of tumor cells that stain positive for SSRP1,
   wherein the subject's tumor is characterized as having a high level of cancer aggressiveness when at least 5% or greater of the tumor cells stain positive for SSRP1; and
   (c) administering an effective amount of a therapy to the subject when the subject's tumor has been classified into the high level of cancer aggressiveness, wherein the therapy comprises neoadjuvant and/or adjuvant therapy.

* * * * *